US012793200B2

(12) United States Patent
Sanders et al.

(10) Patent No.: US 12,793,200 B2

(45) Date of Patent: Nov. 10, 2026

(54) METHODS AND SYSTEM FOR PERFORMANCE ASSESSMENT OF CLEANING OPERATIONS

(71) Applicant: Ecolab USA Inc., St. Paul, MN (US)

(72) Inventors: Jan Sanders, Zaventem (BE); Fernanda Furtado de Melo Albino, Monheim am Rhein (DE); Sabine Swoboda, Langenfeld (DE); Sebastian Niebur, Moenchengladbach (DE); Nadine Göhring, Cologne (DE); Ann Mangskau, St. Louis Park, MN (US); Carola Stingl, Dusseldorf (DE); Daniel D. Anderson, Eagan, MN (US); Florian M. Witt, Wentorf (DE); Christian Lührs, Hamburg (DE); Andreas Krohn, Hamburg (DE); Marc Delling, Hamburg (DE)

(73) Assignee: Ecolab USA Inc., St. Paul, MN (US)

(*) Notice: Subject to any disclaimer, the term of this patent is extended or adjusted under 35 U.S.C. 154(b) by 178 days.

(21) Appl. No.: 18/923,220

(22) Filed: Oct. 22, 2024

(65) Prior Publication Data

US 2025/0045902 A1 Feb. 6, 2025

Related U.S. Application Data

(60) Continuation of application No. 18/497,625, filed on Oct. 30, 2023, now Pat. No. 12,141,957, which is a (Continued)

(51) Int. Cl.

*G06T 7/00* (2017.01)

*A61L 2/24* (2006.01)

(Continued)

(52) U.S. Cl.

CPC .............. *G06T 7/0004* (2013.01); *A61L 2/24* (2013.01); *A61L 2/28* (2013.01); *G01N 21/78* (2013.01);

(Continued)

(58) Field of Classification Search

None

See application file for complete search history.

(56) References Cited

U.S. PATENT DOCUMENTS

| | | | |
|---|---|---|---|
| D227,117 | S | 6/1973 | Breger |
| D427,315 | S | 6/2000 | Saltzstein et al. |

(Continued)

FOREIGN PATENT DOCUMENTS

| | | | |
|---|---|---|---|
| CA | 2541480 | A1 | 9/2006 |
| CN | 107485356 | A | 12/2017 |

(Continued)

OTHER PUBLICATIONS

Notice of Intent to Grant and Text Intended to Grant from counterpart European Application No. 19182688.2 dated Sep. 11, 2025, 102 pp.

(Continued)

*Primary Examiner* — Phuoc Tran

(74) *Attorney, Agent, or Firm* — Shumaker & Sieffert, P.A.

(57) ABSTRACT

The present disclosure relates to a process and a system for assessing the performance of cleaning operations by utilizing an automatic read out routine for test strips subjected to a cleaning operation. Furthermore, the present disclosure relates to a computer program product capable of performing the process.

20 Claims, 30 Drawing Sheets

Related U.S. Application Data continuation of application No. 17/812,904, filed on Jul. 15, 2022, now Pat. No. 11,803,957, which is a continuation of application No. 16/987,868, filed on Aug. 7, 2020, now Pat. No. 11,393,083, which is a division of application No. 16/148,628, filed on Oct. 1, 2018, now Pat. No. 10,762,617.

(60) Provisional application No. 62/567,687, filed on Oct. 3, 2017.

(51) Int. Cl.

| | |
|---|---|
| ***A61L 2/28*** | (2006.01) |
| ***G01N 21/78*** | (2006.01) |
| ***G01N 21/84*** | (2006.01) |
| ***H04N 23/54*** | (2023.01) |
| ***H04N 23/57*** | (2023.01) |
| *G01N 21/77* | (2006.01) |
| *H04N 23/56* | (2023.01) |

(52) U.S. Cl.

CPC ......... *G01N 21/8483* (2013.01); *H04N 23/54* (2023.01); *H04N 23/57* (2023.01); *A61L 2202/14* (2013.01); *G01N 2021/7759* (2013.01); *G06T 2207/10024* (2013.01); *G06T 2207/30108* (2013.01); *G06T 2207/30242* (2013.01); *H04N 23/56* (2023.01)

(56) References Cited

U.S. PATENT DOCUMENTS

| | | | |
|---|---|---|---|
| 6,463,940 | B1 | 10/2002 | Thomas et al. |
| 6,615,850 | B1 | 9/2003 | Hornung |
| 7,437,213 | B2 | 10/2008 | Batcher |
| D605,588 | S | 12/2009 | Nomi et al. |
| D677,669 | S | 3/2013 | Liu |
| D699,246 | S | 2/2014 | Ringlein |
| D715,284 | S | 10/2014 | Iwamoto |
| 9,041,985 | B2 | 5/2015 | Kasahara et al. |
| D730,886 | S | 6/2015 | Tseng |
| 9,289,107 | B2 | 3/2016 | Ellingson et al. |
| 9,329,159 | B2 | 5/2016 | Walicki |
| D768,138 | S | 10/2016 | Malsan |
| 9,473,653 | B2 | 10/2016 | Hayashi |
| D788,778 | S | 6/2017 | Magi et al. |
| D795,323 | S | 8/2017 | Melamed et al. |
| D808,947 | S | 1/2018 | Taniho et al. |
| D837,180 | S | 1/2019 | Silva |
| 10,514,339 | B2 | 12/2019 | Chen et al. |
| D872,072 | S | 1/2020 | Anderson |
| 10,529,219 | B2 | 1/2020 | Herdt et al. |
| 10,667,694 | B2 | 6/2020 | Khosravi et al. |
| 10,762,617 | B2 | 9/2020 | Sanders et al. |
| 11,393,083 | B2 | 7/2022 | Sanders et al. |
| 11,803,957 | B2 | 10/2023 | Sanders et al. |
| 12,133,619 | B2 | 11/2024 | McGinness et al. |
| 12,141,957 | B2 | 11/2024 | Sanders et al. |
| 2005/0201898 | A1 | 9/2005 | Borich et al. |
| 2006/0222567 | A1 | 10/2006 | Kloepfer et al. |
| 2008/0267445 | A1 | 10/2008 | Capewell |
| 2010/0205819 | A1 | 8/2010 | Ashrafzadeh et al. |
| 2011/0209729 | A1 | 9/2011 | Beaudet et al. |
| 2011/0291830 | A1 | 12/2011 | Kaiser |
| 2011/0320133 | A1 | 12/2011 | Mehus et al. |
| 2012/0138092 | A1 | 6/2012 | Ashrafzadeh et al. |
| 2014/0041688 | A1 | 2/2014 | Maennle et al. |
| 2014/0218385 | A1 | 8/2014 | Carmi |
| 2015/0233898 | A1 | 8/2015 | Chen et al. |
| 2016/0171690 | A1 | 6/2016 | Adiri et al. |
| 2017/0023542 | A1* | 1/2017 | Wang .................. H04N 5/2257 |
| 2018/0330338 | A1 | 11/2018 | Holden et al. |
| 2019/0244375 | A1 | 8/2019 | Choi et al. |
| 2021/0019874 | A1 | 1/2021 | Sanders et al. |
| 2021/0076898 | A1 | 3/2021 | Smith et al. |
| 2021/0161355 | A1 | 6/2021 | Rahn et al. |

FOREIGN PATENT DOCUMENTS

| | | | |
|---|---|---|---|
| CN | 107729816 | A | 2/2018 |
| CN | 10367898 | A | 10/2019 |
| CN | 110367898 | A | 10/2019 |
| CN | 107421918 | B | 12/2019 |
| DE | 102008042290 | A1 | 3/2010 |
| DE | 102010033016 | A1 | 2/2012 |
| DE | 102018108775 | A1 | 10/2019 |
| EP | 1272093 | A2 | 1/2003 |
| EP | 1887443 | A1 | 2/2008 |
| EP | 2497404 | A1 | 9/2012 |
| EP | 3088593 | A1 | 11/2016 |
| JP | 05115418 | A | 5/1993 |
| WO | 9930843 | A1 | 6/1999 |
| WO | 0110472 | A1 | 2/2001 |
| WO | 0178573 | A2 | 10/2001 |
| WO | 0213136 | A2 | 2/2002 |
| WO | 2006097294 | A1 | 9/2006 |
| WO | 2007081004 | A1 | 7/2007 |
| WO | 2010118124 | A2 | 10/2010 |
| WO | 2011048575 | A2 | 4/2011 |
| WO | 2011089094 | A1 | 7/2011 |
| WO | 2014137540 | A1 | 9/2014 |
| WO | 2015036311 | A1 | 3/2015 |
| WO | 2015127547 | A1 | 9/2015 |
| WO | 2017056002 | A1 | 4/2017 |

OTHER PUBLICATIONS

Response to Communication pursuant to Article 94(3) EPC dated Dec. 10, 2024, from counterpart European Application No. 19182688.2 filed Feb. 3, 2025, 66 pp.
"CDWA Cleaning Indicator—Cleaning Performance Test," Terragene, retrieved on Feb. 13, 2019, from https://fontlab2000.com/sites/default/files/cdwa-rev.15.pdf, 2 pp.
"NSF/ANSI 3—2017-Commercial Warewashing Equipment," NSF International, ANSI Standard, Apr. 11, 2017, 42 pp.
"Two-Class Logistic Regression," retrieved from https://docs.microsoft.com/en-us/azure/machine-learning/studio-module-reference/two-class-logistic-regression, May 6, 2019, 7 pp.
Powered for iPhone: Wireless Charging Stand for iPhone 8 and Above, Logitech POWERED iPhone Wireless Charging Standard, retrieved from https://www.logitech.com/en-us/productlpowered-iphone-wireless-charging?crid=1537 on Mar. 4, 2019, 10 pp.
Brownlee, "A Tour of Machine Learning Algorithms," machinelearningmastery.com, Aug. 14, 2020, 11 pp.
Communication pursuant to Article 94(3) EPC from counterpart European Application No. 19182688.2 dated Dec. 10, 2024, 4 pp.
Communication pursuant to Article 94(3) EPC from counterpart European Application No. 19182688.2 dated Jan. 30, 2023, 4 pp.
Communication pursuant to Article 94(3) EPC from counterpart European Application No. 19182688.2 dated Oct. 12, 2024, 4 pp.
Communication pursuant to Response as filed May 8, 2020 to Rule 94(3) EPC for counterpart EP application No. 18197940.2 dated May 25, 2020, 4 pp.
Examination Report from counterpart European Application No. 18197940.2 dated Nov. 5, 2021, 4 pp.
Examination Report from counterpart European Application No. 18197940.2, dated Jan. 10, 2020, 4 pp.
Examination Report from counterpart European Application No. 18197940.2, dated Jan. 20, 2021, 4 pp.
Examination Report from counterpart European Application No. 18197940.2, dated May 17, 2021, 4 pp.
Examination Report from counterpart European Application No. 18197940.2, dated Sep. 10, 2020, 5 pp.
Examination Report from counterpart European Application No. 19182688.2, dated Jul. 13, 2021,4 pp.
Examination Report from counterpart European Application No. 19182688.2, dated Jun. 18, 2020, 4 pp.

(56) References Cited

OTHER PUBLICATIONS

Examination Report from counterpart European Application No. 19182688.2, dated Mar. 5, 2021, 5 pp.
Examination Report from counterpart European Application No. 19182688.2, dated Oct. 26, 2020, 4 pp.
Extended Search Report from counterpart European Application No. 18197940.2, dated May 6, 2019, 10 pp.
Extended Search Report from counterpart European Application No. 19182688.2, dated Oct. 1, 2019, 6 pp.
Kumar et al., "A Detailed Review of Feature Extraction in Image Processing Systems," 2014 Fourth International Conference on Advanced Computing & Communication Technologies, Feb. 8, 2014, 8 pp.
Narkhede, "Understanding AUC—ROC Curve," towardsdatascience.com, Jun. 26, 2018, 7 pp.
Narkhede, "Understanding Confusion Matrix," towardsdatascience.com, May 9, 2018, 6 pp.
Notice of Intent to Grant and Text Intended to Grant from counterpart European Application No. 18197940.2 dated May 12, 2023, 74 pp.
Partial Search Report from counterpart European Application No. 18197940.2, dated Jan. 31, 2019, 12 pp.
Patel, "Machine Learning Algorithm Overview," medium.com, Jul. 21, 2018, 10 pp.
Prosecution History from U.S. Appl. No. 16/148,628, dated Jan. 15, 2020 through Jul. 22, 2020, 23 pp.
Prosecution History from U.S. Appl. No. 16/987,868, dated Sep. 16, 2021 through Apr. 29, 2022, 30 pp.
Prosecution History from U.S. Appl. No. 17/812,904, dated Aug. 16, 2022 through Jul. 10, 2023, 26 pp.
Prosecution History from U.S. Appl. No. 18/497,625, dated Jul. 3, 2024 through Oct. 2, 2024, 14 pp.
Prosecution History from U.S. Appl. No. 29/621,149, dated Mar. 19, 2019 through Sep. 6, 2019, 28 pp.
Response to Communication pursuant to Article 94(3) EPC dated Jan. 30, 2023, from counterpart European Application No. 19182688.2 filed May 17, 2023.
Response to Communication pursuant to Article 94(3) EPC dated Nov. 5, 2021, from counterpart European Application No. 18197940.2 filed Jan. 28, 2022, 12 pp.
Response to Examination Report dated Jan. 20, 2021, from counterpart European Application No. 18197940.2, filed May 6, 2021, 8 pp.
Response to Examination Report dated Jun. 18, 2020, from counterpart European Application No. 19182688.2, filed Oct. 16, 2020, 66 pp.
Response to Examination Report dated Mar. 2, 2021, from Counterpart European Application No. 19182688.2, filed May 17, 2023, 71 pp.
Response to Examination Report dated Oct. 26, 2020, from counterpart European Application No. 19182688.2, filed Feb. 23, 2021, 101 pp.
Response to Examination Report dated Sep. 10, 2020, from counterpart European Application No. 18197940.2, filed Jan. 6, 2021, 7 pp.
Response to Extended Search Report dated Jul. 13, 2021, from counterpart European Application No. 19182688.2, filed Nov. 9, 2021,71 pp.
Response to Extended Search Report dated Mar. 2, 2021, from counterpart European Application No. 19182688.2, Filed Jul. 1, 2021, 69 pp.
Response to Extended Search Report dated May 6, 2019, from counterpart European Application No. 18197940.2, filed Jun. 27, 2019, 21 pp.
Response to Rule 94(3) EPC as filed for counterpart EP application No. 18197940.2 filed May 8, 2020, 87 pp.
Saslow, "Collinearity—What it Means, Why its Bad, and How Does it Affect Other Models," medium.com, Jul. 11, 2018, 5 pp.
Shung, "Accuracy, Precision, Recall or F1?," towardsdatascience.com, Mar. 15, 2018, 7 pp.
Singh, "Model-Based Feature Importance," towardsdatascience.com, Jan. 3, 2019, 7 pp.
YouTube, "Regularization Part 1: Ridge (L2) Regression," retrieved from https://www.youtube.com/watch?app=desktop&v=Q81RR3yKn30&t=3s, Sep. 24, 2018, 1 pp.
YouTube, "Regularization Part 2: Lasso (L1) Regression," Retrieved from https://www.youtube.com/watch?app=desktop&v=NGf0voTMIcs, Oct. 1, 2018, 1 pp.

* cited by examiner

A B

A B

METHODS AND SYSTEM FOR PERFORMANCE ASSESSMENT OF CLEANING OPERATIONS

This application is a continuation of U.S. patent application Ser. No. 18/497,625, filed Oct. 30, 2023, which is a continuation of U.S. patent application Ser. No. 17/812,904, filed Jul. 15, 2022, and issued as U.S. Pat. No. 11,803,957, which is a continuation of U.S. patent application Ser. No. 16/987,868, filed Aug. 7, 2020, and issued as U.S. Pat. No. 11,393,083 on Jul. 19, 2022, which is a divisional of U.S. patent application Ser. No. 16/148,628, filed Oct. 1, 2018, and issued as U.S. Pat. No. 10,762,617 on Sep. 1, 2020, which claims the benefit of U.S. Provisional Application No. 62/567,687 filed on Oct. 3, 2017, entitled, "METHODS AND SYSTEM FOR PERFORMANCE ASSESSMENT OF CLEANING OPERATIONS," each of which is incorporated by reference herein in its entirety.

TECHNICAL FIELD

The present disclosure relates to a process and a system for assessing the performance of cleaning operations by utilizing an automatic read out routine for test strips subjected to a cleaning operation. Furthermore, the present disclosure relates to a computer program product capable of performing the process.

BACKGROUND

Based on the progress in chemistry and the evolution in process design cleaning processes has increased in performance particularly over the last decades. New detergent formulations and highly task specific machines has come to market, rendering the overall cleaning processes very efficient and more environmentally friendly. Nevertheless, also the standards for process definition and reproducibility evolved, increasing the burden of documentation. Especially, for GMP-regulated industry sectors there is a high demand for significant process parameter in the field of cleaning, which are able to provide more reliable process information besides the "visually clean" condition provided by the standard.

Several different solutions for the assessment of cleaning performance have been proposed in the area of sterilization, wherein the absolute level of contamination after the process as well as the reduction ability is a critical process parameter. For monitoring purposes the literature propose either to examine directly the status of the surface of items subjected to the cleaning process or to use "artificial" test devices, which are introduced into the process additionally to the items to be cleaned. The latter variant is able to provide reproducible test standards and is more flexible, because different aspects of the cleaning process can be monitored as a function of the test device design.

WO 2014/137540 A1 for instance disclose a method of colorimetrically determining a concentration of at least one chemical species in a liquid medium, the method comprising: providing a chemical test strip having a reactive zone; providing an imaging device and image analyzing software; exposing the reactive zone to at least a portion of the liquid medium thereby creating a post-exposure reactive zone; imaging the post-exposure reactive zone using the imaging device thereby creating a digital image of the post-exposure reactive zone; optionally cropping the digital image of the post-exposure reactive zone to isolate a portion of the digital image for analysis; analyzing at least one colorimetric parameter of at least the portion of the digital image of the post-exposure reactive zone using the image analyzing software to determine the concentration of the at least one chemical species; optionally outputting the determined concentration of the at least one chemical species of the liquid medium; and optionally taking action based on the determined concentration.

Furthermore, WO 2015/036311 A1 disclose a method for determining the cleaning performance of a formulation, in which a) the formulation is provided, b) a test body is brought into contact with the formulation, the test body being contaminated with a protein-containing test contaminant, c) the contaminated test body is left in contact with the formulation in order to clean the contaminated test body, d) the cleaned test body is rinsed, e) if necessary the rinsed test body is dried, f) if necessary the test contaminant remaining on the test body is evaluated in terms of quality and g) the test contaminant remaining on the test body is analyzed in terms of quantity, the quantitative analysis of the remaining test contamination including the removal of the remaining test contaminant from the test body.

Nevertheless, albeit the existence of several monitoring alternatives, there is still the need for further processes, which can be used in the background of industrial working conditions and which are able to deliver reproducible results with a high sensitivity.

SUMMARY

In one example, the disclosure is directed to a process for the performance assessment of cleaning operations at least comprising the steps of:

a) exposing at least one chemical test strip comprising a carrier and an indicator means, wherein the indicator means comprises at least in a defined surface area a color indicator, to the chemical environment of a cleaning operation;
b) recording with an image device the data of at least one digital color image of the test strip after the cleaning operation; and
c) quantitative evaluation of the digital image data, characterized in that the quantitative evaluation of the digital color image data in step c) at least comprises the steps c1) to c5):

c1) color-to-greyscale image data transformation;
c2) glare detection;
c3) greyscale- to binary image data transformation;
c4) image pixel-area normalization; and step
c5) pixel-counting, wherein the number of black and white pixels of the test strip image data after the cleaning process are counted and the counting result is compared to the quantitative evaluation result of the test strip prior to the cleaning process.

In some examples, in step c1) the color-to-greyscale transformation may include a luminescence RGB-color-to-greyscale data transformation according to the following equation $$Y = 0.299R + 0.587G + 0.114B,$$

wherein Y is the resulting greyscale- and R, G, B are the RGB-values of the color pixel, respectively.

In some examples, the greyscale- to binary image data transformation in step c3) may be achieved by an adaptive threshold transformation.

In some examples, the adaptive threshold transformation in step c3) may be achieved by the following mathematical function $$dst(x, y) = \begin{cases} 255 & \text{if } src(x, y) > T(x, y) \\ 0 & \text{otherwise} \end{cases}$$

wherein dst(x,y) is the binary result of the transformation, src(x,y) the greyscale-value of the pixel(x,y) and T(x,y) an individual pixel threshold value, wherein the individual pixel threshold value is calculated from the mean greyscale-value of the pixel neighborhood minus a constant C.

In some examples, the mean greyscale-value of the pixel neighborhood may be calculated from a 251×251 matrix around the pixel(x,y) and the constant C is 5.

In some examples, the glare detection in step c2) may at least comprise the transformation of the digital color image data into a HSV-color domain and performing a glare detection based on the V(x,y)-value of individual pixels or pixel areas.

In some examples, image spots larger than 10×10 pixels may be excluded from further evaluation if all pixels within the spot comprise V(x,y)-values larger than 95% of the maximum V-value of the digital image.

In some examples, the image pixel-area normalization in step c4) may be based on an image recognition process of the binary image obtained in step c3), wherein the chemical test strip comprises additional lines surrounding the indicator area and only the pixel area between the lines contribute to the quantitative evaluation of the digital image.

In some examples, the image pixel-area normalization in step c4) may be based on an image recognition process of the binary image obtained in step c3), wherein the chemical test strip comprises additional lines of equal length connected in the form of a geometrical body and only the pixel area within the geometrical body contribute to the quantitative evaluation of the digital image.

In some examples, a mathematical transformation of the number of black and white pixel of the test strip image data obtained in step c5) may be performed at least comprising the calculation of a black to white pixel ratio and, in a step d), a further grouping of the mathematical transformation result in quality classes is carried out.

In some examples, based on the result of the grouping in step d) an action plan may be selected.

In another example, the disclosure is directed to a system for the performance assessment of cleaning operations, the system comprises at least:

- a chemical test strip having a reactive zone, the reactive zone is operable to change color as a function of a cleaning process;
- a chemical test strip receptacle forming an imaging chamber to provide uniformity in lighting and distance between the imaging device and the chemical test strip during imaging of the reactive zone;
- an imaging device capable of creating a digital image of the reactive zone of the chemical test strip after the reactive zone has been exposed to the cleaning process;
- image analyzing software adapted to analyze at least one colorimetric parameter of the digital image of the test strip reactive zone according to a process of any one of examples 1-11.

In some examples, the test strip comprises at least two separated reactive zones of the same chemical composition.

In some examples, the test strip comprises at least three separated reactive zones of the same or different chemical composition, wherein the surface area ratio of reactive zone to total surface area of the test strip is larger or equal 0.5 and smaller or equal to 0.9.

In some examples, the test strip comprises additional lines in the form of a geometrical body, wherein the body is selected from the group consisting of parallelogram, hexagon or circle, and the surface area ratio of reactive zone to total surface area within the geometrical body is larger or equal 0.7 and smaller or equal to 0.95.

In another example, the disclosure is directed to a computer program product adapted to perform the process according to any of the above described examples.

In another example, the disclosure is directed to an imaging box for use in an image capture procedure for the performance assessment of cleaning operations, comprising a housing defined by a front surface and a back surface and forming an interior cavity when the housing is placed on a substantially flat surface, the front surface having a receptacle configured to receive a mobile device, the front surface further including at least one camera aperture configured to correspond to the position of a camera lens of the mobile device when the mobile device is received in the receptacle, the back surface including a test strip slot configured to receive and hold a chemical test strip comprising a carrier and an indicator means in a substantially flat position, the back surface further including a test strip aperture configured to correspond to the position of a chemical test strip when received into the test strip slot, such that an image of the chemical test strip may be captured by the camera of the mobile device when the chemical test strip is inserted into the test strip slot such that the indicator means is facing the interior cavity of the housing.

In some examples, the front surface of the housing may further include a flash aperture configured to correspond to the position of a light emitting flash of the mobile device when the mobile device is received in the receptacle.

In some examples, the imaging box may further include at least one diffusing rib positioned within the interior cavity of the housing to diffuse light emitted from the flash of the mobile device.

In some examples, the imaging box may further include a light source positioned within the interior cavity of the housing.

In some examples, the imaging box may further include a cord management slot or aperture in the front surface of the housing configured to receive a charging cable of the mobile device.

In some examples, the imaging box may further include a light covering sticker sized to cover at least part of the front surface of the housing and having an aperture positioned to correspond to the camera aperture in the front surface of the imaging box.

In another example, the disclosure is further directed to a system comprising an imaging box for use in an image capture procedure for the performance assessment of a cleaning process, the imaging box comprising a housing defined by a front surface and a back surface and forming an interior cavity when the housing is placed on a substantially flat surface, the front surface having a receptacle configured to receive a mobile device, the front surface further including at least one camera aperture configured to correspond to the position of a camera lens of the mobile device when the mobile device is received in the receptacle, the back surface including a test strip slot configured to receive and hold a chemical test strip comprising a carrier and an indicator means in a substantially flat position, the back surface further including a test strip aperture configured to correspond to the position of a chemical test strip when received into the test strip slot, such that an image of the chemical test strip may be captured by the camera of the mobile device when the chemical test strip is inserted into the test strip slot such that the indicator means is facing the interior cavity of the housing, a computing device configured to receive and evaluate the digital image of the chemical test strip and generate an assessment of the performance of the cleaning process, and an application running on the mobile device configured to display the assessment of the performance of the cleaning process.

In some examples, the computing device may be located remotely with respect to the mobile device.

In some examples, the application running on the mobile device may be further configured to guide a user through a chemical test strip image capture procedure.

It should be noted that, as used in this specification and the appended claims, the singular forms “a”, “an”, and “the” include plural referents unless the content clearly dictates otherwise. Thus, for example, reference to a composition containing “a compound” includes a composition having two or more compounds.

It should also be noted that the term “or” is generally employed in its sense including “and/or” unless the content clearly dictates otherwise.

It is specifically understood that any numerical value recited herein (e.g., ranges) includes all values from the lower value to the upper value, i.e., all possible combinations of numerical values between the lowest value and the highest value enumerated are to be considered to be expressly stated in this application. For example, if a concentration range is stated as 1% to 50%, it is intended that values such as 2% to 40%, 10% to 30%, or 1% to 3%, etc., are expressly enumerated in this specification. These are only examples of what is specifically intended.

It is to be understood that all values and ranges between values and ranges are encompassed by the methods of the present disclosure.

BRIEF DESCRIPTION OF THE DRAWINGS

The example process and parts of the example system for performing the example process are exemplified in the following figures.

DETAILED DESCRIPTION

Figure 1:
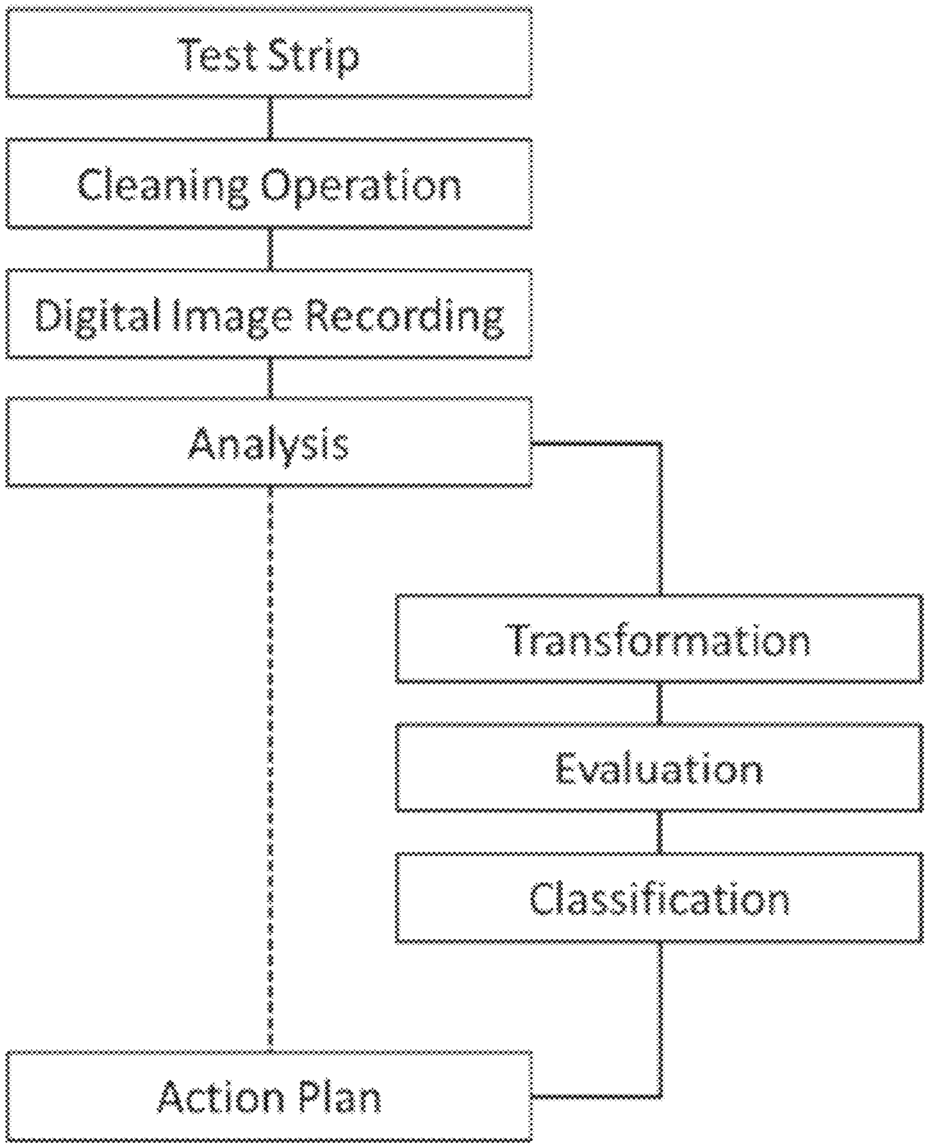
FIG. 1 shows a possible sequence of process steps in the example process.

In one example, the above mentioned task is achieved by an example process for the performance assessment of cleaning operations at least comprising the steps of:

a) exposing at least one chemical test strip comprising a carrier and an indicator means, wherein the indicator means comprises at least in a defined surface area a color indicator, to the chemical environment of a cleaning operation;

b) recording with an image device the data of at least one digital color image of the test strip after the cleaning operation; and c) quantitative evaluation of the digital image data, characterized in that the quantitative evaluation of the digital color image data in step c) at least comprises the steps c1) to c5):

c1) color-to-greyscale image data transformation;

c2) glare detection;

c3) greyscale- to binary image data transformation;

c4) image pixel-area normalization; and step c5) pixel-counting, wherein the number of black and white pixels of the test strip image data after the cleaning process are counted and the counting result is compared to the quantitative evaluation result of the test strip prior to the cleaning process.

Surprisingly it has been found that above mentioned process is able to provide reliable and reproducible quantitative data, which are highly representative to the used cleaning operation. For this purpose a color indicator is used, wherein the amount of the indicator color change is a function of the overall cleaning conditions. Especially, the transformation and evaluation routine delivers quantitative results which are less prone to mistakes or failures during digital image recording and, in addition, the discrimination power between positive or negative results is greatly enhanced compared to other methods of performance evaluation. The overall process is user and resource friendly, and large parts can be performed under expert control. Therefore, risks of systematic errors are reduced.

The overall target of the process is a performance assessment of cleaning operations. This means that the process is able to deliver a quantitative value which is proportional to the performance of overall cleaning process. This may either be performed by a direct comparison of the remaining color indicator area. If the indicator area remains physically or chemically unaltered, the overall cleaning process performance is low, whereas if a large change is detectable as a result of the cleaning process the cleaning process performance is satisfactory. It is especially an advantage of the process that the quantitative result is proportional over a wide range of different cleaning conditions. In several applications, particularly for medical devices, it is also possible that the performance assessment is guided by the same or similar quantitative readout of the test strip (consistency and reproducibility), only. The cleaning power of the process is proven in an earlier stage (during setup or validation stage) and the test strip read-out is assessed with respect to any change over time.

In the process in step a) the chemical test strip is exposed to the chemical environment of a cleaning operation. This means that the test strip is brought in contact with the medium which is used to perform the cleaning operation. The medium may either be a liquid and the test strip is contacted under the same physical conditions, e.g. at the same temperature and for the same time, as is the standard of the cleaning operation under evaluation.

The test strip comprise a carrier and an indicator means, wherein the indicator means comprises at least in a defined surface area a color indicator. In order to quantitatively evaluate the cleaning performance a color change of the indicator area is used. The color change may refer to the action of becoming a different color or a different shade of the same color. The color indicator may be evenly distributed over the carrier surface or it is also possible that only certain areas of the carrier are covered by the indicator. Furthermore, it is possible that the carrier comprise further areas not being coated with the color indicator for instance comprising additional labels, identification marks or further lines which are used within the process. The indicator-color may either fade or a color may evolve as a function of the cleaning process. Suitable color indicators are known to the skilled artisan. The color indicator may be selective to only one chemical substance or only one physical parameter, e.g. temperature, but is also possible that the indicator is able to monitor the presence or absence of more than one chemical substance or several physical parameter. For instance it is possible that the color indicator contains a protein based soil that is representative of the type(s) of soil to be removed from the articles being washed and disinfected. A number of different physical/chemical factors can also be monitored by the test strip, for instance spray pressure, water quality (e.g. water hardness, pH, total dissolved solids (TDS)), detergent dose, surfactant package, enzyme, exposure time, and temperature. The influence of the cleaning process on multiple parameter may include a combination of different indicators, independently changing the color as a function of the parameter of interest. In addition, the indicator area is defined in the meaning that the surface on the test strip coated with the color indicator is fixed and the same for all used test strips. This in contrast to situations, wherein indicator areas are randomly coated on a test strip.

In step b) recording with an image device the data of at least one digital color image of the test strip after the cleaning operation. The image device can be any digital recording means also capable of assessing color information from a subject. The device can for instance be a camera, color or optical density device, a mobile phone, a computer including a hardware scanner device or the like. The digital color image can be in any digital format, preferred are standard image formats like RAW, GIF, PNG, JPEG, TIFF, BMP or the like.

In step c) the digital image data are quantitatively evaluated. It has surprisingly been found that the significance of the test strip read-out can be greatly enhanced if the digital image data are not used as is. Especially, a color-to-greyscale-transformation of the color image data is able to increase the reproducibility and the significance of the quantitative result. This is especially true for a combination of a blue colored test strip and the above mentioned color transformation. A quantitative evaluation in the sense of the disclosure means, that a number will be achieved as the result of the evaluation. Usually the number result will be proportional to the cleaning process performance. The evaluation can either be performed within the memory of the image device or it is also possible that the data are transferred from the image device to a remote server, where the further processing and calculations are performed. This might help to control the data transformation and also enables in principle an additional quality control of the process output on the remote server.

In further steps it is also possible to further classify the quantitative result. Such further classification might increase the user-friendliness of the overall process by the introduction of quality classes, wherein it is possible to relate certain numerical outcomes from the evaluation step into quality classes e.g. the quality classes of "performance is" low, sufficient, high. It is also possible to evaluate an overall process score, wherein the result of the process is mathematically transformed to a %-scale. This may be done by scaling the result with a factor, wherein the factor can be calculated with respect to comparison measurements, wherein for instance no cleaning was achieved and wherein the complete indicator area was removed by the cleaning process.

The quality classification may be performed on a remote server or on the image device. In the first case the classification can be evaluated on the remote server and transmitted at least back to an operator and/or the image device. This means that the numerical results of the evaluation and the classification based thereon are calculated on the remote server and only the result of the process is send back to an operator and/or the image device. The image device is preferably a mobile device, including some graphical capabilities in order to ease the information display. In addition, it is further feasible that the result is send to further remote servers or other computers, if necessary. For instance it is possible that all cleaning operation results of one company are additionally send to a central computer of the company in order to provide a complete overview about the performance of cleaning processes within the company over time. An operator can be the person who handled already the test strip or for instance a quality manager, not directly related to the physical process steps. The transmission or the sending of the image data and/or the quantitative evaluation results to a remote server can be considered an optional final step after performing the evaluation. In addition, by this step it might be possible to also detect systematic changes in the photographing conditions.

Step c1) requests a color-to-greyscale data transformation of the digital image. For this color-to-greyscale transformation every pixel of the image is transferred from a color- (e.g. RGB-) to a greyscale-space. This means that the color information originally present in the digital image is reduced to only one value (usually one byte, 8 Bit, 256 greyscale values). Besides the reduction of the data amount it was surprisingly found that although an overall reduction of data is achieved the significance of the evaluation is greatly enhanced. Without being bound to a theory it is assumed that artifacts and image failures based on wrong image recording conditions are better detectable in a greyscale—instead of a color-domain. This step overall increases the sensitivity and the reproducibility of the readout.

In step c2) a glare detection is performed on the transformed digital image. Besides the greyscale transformation it has been found useful to perform a glare detection step in order to increase the reliability of the overall process. In this step it is possible to rule out artifacts in the images based on unsuitable or unfavorable light-conditions, e.g. obtained under too much light or with light reflections, in the course of image recording. This step is able to identify the parts of the digital image, which are not able to contribute correctly to the right evaluation process outcome based on a saturation of the image device.

In the step c3) the greyscale-image data are transformed into binary image data. Within this step the image data amount is further reduced by restricting the intensity values of the pixels either to one or zero. Such step can for instance be achieved by a simple thresholding algorithm, wherein the threshold value is a global variable that gets applied to every pixel in the image. In addition, more sophisticated methods like adaptive thresholding can be used. In such method the threshold value is calculated for smaller regions of the image and therefore, there will be different threshold values for different regions. Thresholding may for instance be performed by a linear threshold with Otsu's method. At the end of this stage the image becomes a bit-vector suitable for image recognition algorithms.

In step c4) the image pixel-area can be normalized. In order to account for different image recording conditions, and here especially the focal distance between the test strip and the image device, it has been found useful to normalize the pixel area which is used for evaluation. This might be done by image recognition methods, wherein the image comprises additional information, e.g. lines or optically different areas in the picture, indicating the area which is principally able to provide information for evaluation. Within this step certain areas of the image can be excluded from evaluation, for instance areas outside a defined indicator area not including any relevant content. In addition, to this normalization step it is further possible to generate from the usable pixel-number a scaling factor, accounting for different usable pixel-areas in different measurements. Such scaling factor is able to increase the inter-comparability between different measurements.

In the last process step c5) a pixel-counting is performed, wherein the number of black and white pixels of the test strip image data after the cleaning process are counted and the counting result is compared to the quantitative evaluation result of the test strip prior to the cleaning process. In the pixel counting the total number of black and white pixels are assessed. For this calculation either the complete transformed image may be used or only certain fractions of the image. For instance all detected set (black) and unset (white) pixels can be counted separately and the ratio can be calculated. Therefore, the calculation of the ratio can deliver further information with respect to the validity of the recoded image. Furthermore, a completely empty (0) result can also be considered an error and discarded, because due to noise there should always be some detected pixels. Thus, a ratio of <0.0001 points can for instance also be attributed to a faulty or full saturated sensor and can be discarded. The ratio can be further normalized, e.g. by using a further calibration value to achieve a value between 0 and 100, which can be presented to the operator/user to the user.

Within a first example embodiment of the process in step c1) the color-to-greyscale transformation can be a luminescence RGB-color-to-greyscale transformation according to the following equation $$Y=0.299R+0.587G+0.114B,$$

wherein Y is the resulting greyscale- and R, G, B are the RGB-values of the color pixels, respectively. Surprisingly it has been found useful to perform a special greyscale transformation routine. This routine has been able to deliver reproducible and significant values for a cleaning process. This evaluation results are surprisingly better compared to other greyscale-transformations like e.g. principal component analysis (PCA) or its kernel generalization (w.r.t., kernel PCA, KPCA) or Intensity- or Gleam-transformations. This luminescence transformation achieves very reproducible results and the influence of the recording conditions is much smaller compared to the other transformations. The pixel counting results are statistically better and allow better evaluation of the cleaning process. The latter is especially true for test strips comprising blue tinted indicator areas.

In a further example embodiment of the process the greyscale- to binary image data transformation in step c3) can be achieved by an adaptive threshold transformation. The use of an adaptive thresholding routine delivers better results with respect to reproducibility and accuracy. This effect can at least in part be based on the fact that the test strip might not be evenly luminated or that the test strip might also comprise different surface areas comprising different optical properties. In these cases an adaptive thresholding routine can yield better results, because the optical properties of the surrounding pixel are included in the calculation.

In a preferred characteristic of the process the adaptive threshold transformation in step c3) is achieved by the following mathematical function $$dst(x,y)=\begin{cases}255 & \text{if } src(x,y)>T(x,y)\\ 0 & \text{otherwise}\end{cases}$$

wherein dst(x,y) is the binary result of the transformation, src(x,y) the greyscale-value of the pixel(x,y) and T(x,y) an individual pixel threshold value, wherein the individual pixel threshold value is calculated from the mean greyscale-value of the pixel neighborhood minus a constant C. It was found that for image transformation from greyscale to black/white an adaptive threshold results in a better and more reproducible and accurate quantification of the pixel. This might be attributable to the fact that the test strip might comprise different surfaces, wherein the different surfaces might comprise different optical properties like reflectance. In such cases an adaptive threshold mechanism might be able to compensate for optical effects not related to washing/cleaning processes.

In another aspect of the process the mean neighborhood greyscale value can be calculated from a 251×251 matrix around the pixel(x,y) and the constant C is 5. For a majority of different test strip sizes and test strip designs and different image recording devices it has been found suitable to use above mentioned parameter for the adaptive thresholding algorithm. These parameters do not over-emphasize the heterogeneity of the different test strip areas and result in better reproducible pixel count outcomes.

In another example embodiment of the process the glare detection in step c2) may at least comprise transformation of the digital color image into a HSV-color domain and performing a glare detection based on the V(x,y)-value of individual pixels or pixel areas. For this step the original color camera image is transformed in the HSV color domain, wherein the V (value) in this domain represents an absolute value independent from color and saturation. The higher V is the brighter the pixel is. Due to noise it is unlikely that there are large regions of evenly high V. If this occurs it most probably means that the image device sensor (e.g. a camera) is saturated due to too much light or reflections. If the sensor is saturated false results are obtained.

In a further aspect of the process image spots larger than 10×10 pixels can be excluded from further evaluation if all pixels within the spot comprise V(x,y)-values larger than 95% of the maximum V-value of the digital image. Above mentioned values has proven to yield “right” and reproducible results for the glare detection process. Setting the V-limit for larger pixel areas might increase the risk of taking into account image pixel areas, wherein a glare influence is already present and smaller pixel areas might result in a false exclusion of significant pixel areas from the process.

According to a further example embodiment of the process the image pixel-area normalization in step c4) is based on an image recognition process of the binary image obtained in step c3), wherein the chemical test strip comprises additional lines surrounding the indicator area and only the pixel area between the lines contribute to the quantitative evaluation of the digital image. The incorporation of further optimal marks or flags on the test strip has shown to be able to improve the automatic read out routine and the overall transformation process. It is possible to enhance the significance of the counting and also to detect further operator-related digital image faults. This is for instance the case, if no lines can be detected in the picture. In this case either an empty image is evaluated or a wrong test strip used. Therefore, this example embodiment is able to increase further the reliability of the overall process.

In another characteristic of the process the image pixel-area normalization in step c4) can be based on an image recognition process of the binary image obtained in step c3), wherein the chemical test strip comprises additional lines of equal length connected in the form of a geometrical body and only the pixel area within the geometrical body contribute to the quantitative evaluation of the digital image. Especially the combination of a highly symmetric image recognition pattern encompassing the color test strip is able to detect further failure in the image recording process and thus is able to render the overall process more failure proof. The geometrical body may for instance be selected from the group consisting of triangle, acute triangle, equilateral triangle, isosceles triangle, obtuse triangle, rational triangle, right triangle, 30-60-90 triangle, isosceles right triangle, Kepler triangle, scalene triangle, quadrilateral, cyclic quadrilateral, square, kite, parallelogram, rhombus (equilateral parallelogram), Lozenge, rhomboid, rhomb, rectangle, square (regular quadrilateral), rectagon, quadrangle, quadragon, tangential quadrilateral, trapezus, trapezoid, isosceles trapezoid, pentagon, regular pentagon, pentagonoid, hexagon, Lemoine hexagon, heptagon, octagon, regular octagon, nonagon, decagon, regular decagon, hendecagon, dodecagon, hexadecagon, icosagon, star without crossing lines, star polygon, hexagram, star of David, heptagram, octagram, star of Lakshmi, decagram or a pentagram. The hexagon or the parallelogram for image recognition are preferred, because the length of the lines and the angle between the corners can also be used for evaluation purposes. Hence, it is also possible to detect angular distortions in the image, wherein the distortions might be caused by operator failure in positioning the test strip prior to image recording. Additionally, also the use of a circle or an ellipse is preferred, because such structures are highly symmetrical and can be used to further detect image distortions.

In addition, it is possible that chemical test strip comprises additional lines of equal length connected in the form of a geometrical body and the geometrical body is a circle. The circle is considered to be constructed from a very large number of very small lines forming the circle. Especially, the geometrical form of a circle can help to obtain better evaluation results, because optical distortions in the image can easily be detected.

Within a further aspect of the process a mathematical transformation of the number of black and white pixel of the test strip image data obtained in step c5) can be performed, at least comprising the calculation of a black to white pixel ratio and, in a step d), a further grouping of the mathematical transformation result in quality classes can be carried out. Besides the total number of black or white pixels it has been found useful to base the overall classification on the ratio of black and white pixels. This process step renders the overall process more failure proof. In part this can be addressed to the fact that a ratio is less sensitive to image-size failures compared to taking into account an absolute pixel count value. In addition, the further grouping of process outcomes in quality classes, like "pass", "fail", "unchanged", "process changed", or the like, may further increase the user-friendliness of the overall process.

In an example embodiment of the process based on the result of the grouping in step d) an action plan can be selected. Besides just reporting the overall outcome of the evaluation it is further possible to pass further instructions or advice back to the device or another person/operator. Such instructions in the action plan may for instance comprise the advice of increase or lower the detergent concentration, raise or lower the temperature or process time, use a different detergent, control or change water quality, i.e. hardness and so on.

In addition to the process also a system for the performance assessment of cleaning operations is in the scope of the disclosure, wherein the system comprises at least:

a chemical test strip having a reactive zone, the reactive zone operable to change color as a function of a cleaning process;

a chemical test strip receptacle forming an imaging chamber to provide uniformity in lighting and distance between the imaging device and the chemical test strip during imaging of the reactive zone;

an imaging device capable of creating a digital image of the reactive zone of the chemical test strip after the reactive zone has been exposed to the cleaning process image analyzing software adapted to analyze at least one colorimetric parameter of the digital image of the test strip reactive zone according to the example process. Surprisingly it has been found that above described system is able to reliably assess the cleaning performance of liquid as well of gaseous cleaning operations and provide a reproducible numerical result, wherein especially the latter can be used to classify the overall cleaning process and to propose further actions based on the result. For further advantages of the example system it is explicitly referred to the example process.

The chemical test strip comprises a reactive zone. This means that the chemical test strip have at least one reactive zone that changes color upon exposure to a particular chemical species, present in the cleaning liquid or gas. In another example embodiment of the chemical test strip have at least one reactive zone that changes shade of a color (i.e., color intensity). In certain exemplary embodiments, the chemical test strip may test for the presence or concentration of a soluble impurity present in the liquid medium. In certain exemplary embodiments, the chemical test strip may test for the presence or concentration of a soluble treatment chemical in the liquid medium. Non-limiting examples of chemical test strips include those that are able to test for presence or concentration of tensides, dissolved calcium, acidity (i.e., pH), concentration of total hardness, chloride concentration, total residual chloride, free chloride residual, ortho-phosphate, m-alkalinity, and p-alkalinity. In certain exemplary embodiments, the chemical test strips are able to test for the presence and/or concentration of one or more treatment chemicals. Non-limiting examples of such test strips include those that test for the presence and/or concentration of an anionic, non-ionic or cationic tenside, enzymes, corrosion inhibitor, polymers, a biocide, and combinations thereof. In addition, it is possible that the reaction zone is removed, e.g. washed away, from the test strip by the cleaning operation. In such cases the cleaning result is better if less indicator is present on the strip after the cleaning process. Therefore, the mathematical calculation may be reversed in such cases. Nevertheless, it is also possible to check for the run-to-run consistency of the overall cleaning process only, by just comparing the read-outs of the single processes.

A cleaning process includes the activity of removing dust, soil, or any substance that makes a surface not clean from objects and places. The cleaning process monitored by the example process is especially performed in closed automated surroundings, e.g. a dish-washer, washing machines or sterilization chambers and usually include the use of cleaning means in the form of liquid (aqueous) cleaning compositions or for instance the use of gases or gas plasmas to achieve cleaning. In addition, the example routine can also be used to monitor the automated cleaning of surfaces, such as performance monitoring of robots wiping floors or the like.

The chemical test strip may also comprise a chemical test strip receptacle. The receptacle is a physical mean for placing the test strip securely within the recording process step. The receptacle also forms at least a part of an imaging chamber in order to provide uniformity in lighting and distance between the imaging device and the chemical test strip during imaging of the reactive zone. The receptacle further enhances the read-out stability of the test strip. In addition, it is also feasible to provide further physical means, which are able to securely position the test strip in the course of the cleaning process and to use the same physical means for placing the test strip within the imaging chamber. Especially, the latter is able to simplify the overall handling of the test strip.

An imaging chamber may be a box-shaped device that has one side open. The open side may be covered by an imaging device adaptor. The box may be built either as a one or more, e.g. two or three, part device. The task of the box is to generate a defined physical surrounding for image recording. Therefore, the chamber will especially control the incoming light and the distance between test strip and image device.

For the imaging device any digital means can be used, being capable of recording a digital image and also capable of hosting a software and interaction with a remote server. In certain exemplary embodiments, the imaging device is a hand held device. In certain exemplary embodiments, the hand held device weighs no more than 500 g. In certain exemplary embodiments, creation of the digital image is carried out in typical fashion using a digital camera of any type. In certain exemplary embodiments, the digital camera is a hand held digital camera. In certain exemplary embodiments, the digital camera is incorporated into or otherwise operably attached to a mobile device (e.g., a mobile phone, tablet, media player, etc.). In certain exemplary embodiments, the digital camera is incorporated into or otherwise operably attached to a tablet device. In certain exemplary embodiments, the digital camera is incorporated into or otherwise operably attached to a computer. In certain exemplary embodiments, the computer is a desktop computer. In certain exemplary embodiments, the computer is a laptop computer.

In certain exemplary embodiments, the image is transmitted via a network, such as a cellular network or the Internet from the image device. For some exemplary embodiments, the image device may provide also image analyzing software including a user interface in the form of an "app" or the like. In certain exemplary embodiments, the app may perform one or more of the following functions: enable storage of data and/or analysis thereof, upload data and/or analysis thereof to a central server or other specified location, provide "geo-tagging" of data and/or analysis thereof, and recommend a plan of action (as described herein). In certain exemplary embodiments, the app may generate reports that illustrate, describe, and/or summarize the data and/or analysis thereof. In certain exemplary embodiments, the app may perform and report statistical analysis calculations related to the data and/or analysis thereof.

In an example embodiment of the system the test strip may comprise at least two separated reactive zones of the same chemical composition. For controlling the reliability of the process outcome it has been found useful to use at least two separated reactive zones instead of just one continuous reactive zone. Especially during image processing and evaluation the two reactive zones can be used for cross-checking routines, which are able to improve the failure resistance of the overall process.

In a further example embodiment of the system the test strip may comprise at least three separated reactive zones of the same or different chemical composition, wherein the surface area ratio of reactive zone to total surface area of the test strip is larger or equal 0.5 and smaller or equal to 0.9. Besides using more than one reactive area on the test strip at has been found advantageous, that the test reactive zone covers the majority of but not the complete test strip area. As discussed above this enable the incorporation of further tags on the test strip which can be used during image recognition. Furthermore, this ratio might be helpful for calibration and cross checking of the digital image area. It is also within the meaning of the disclosure that above given ratio is larger or equal about 0.5 and smaller or equal to about 0.9.

According to another aspect of the system the test strip may comprise additional lines in the form of a geometrical body, wherein the geometrical body is selected from the group consisting of parallelogram, hexagon or circle, and the surface area ratio of reactive zone to total surface area within the geometrical body is larger or equal 0.7 and smaller or equal to 0.95. It has been found useful, that not the complete test strip surface is used for the chemical indicator. The remaining surface can be used for image calibration and, as already explained, the image evaluation routine is more stable if several areas are present, divided by areas wherein no reactive zone are present. In a further example embodiment, the single reactive zones may be separated by one or two zones of the same dimension comprising no reactive zones and no indicator. This set-up may further be advantageous for image recognition purposes. It is also within the meaning of the disclosure that above given ratio is larger or equal about 0.7 and smaller or equal to about 0.95.

In addition to the process and the system also a computer program product adapted to perform the example process is within the scope of disclosure.

FIG. 1 exhibits an example sequence of process steps according to the disclosure directed to evaluate the performance of a cleaning process. In the first step a test strip (step 1) comprising a color indicator is subjected to a cleaning operation (step 2), for instance by placing the test strip into a washing machine. After the cleaning process the test strip is taken out of the machine by an operator and a digital image of the indicator area of the test strip is recorded (step 3). The digital image data may be sent to a remote server or processed on the hand-held device. An analysis of the digital image data is performed (step 4) and may include data transformation steps, like for instance a color transformation, an evaluation of the transformation outcome, e.g. by pixel counting methods and finally a classification step, wherein the evaluation outcome is grouped into different quality classes like for instance pass or fail. The analysis step may include the transformation and evaluation steps depicted in FIG. 2. Finally, it is optionally possible to provide further information based on the classification to the operator (step 8). Such further information may include the advice to change physical or chemical parameter of the cleaning process (e.g. temperature, time, detergent amount).

Figure 2:
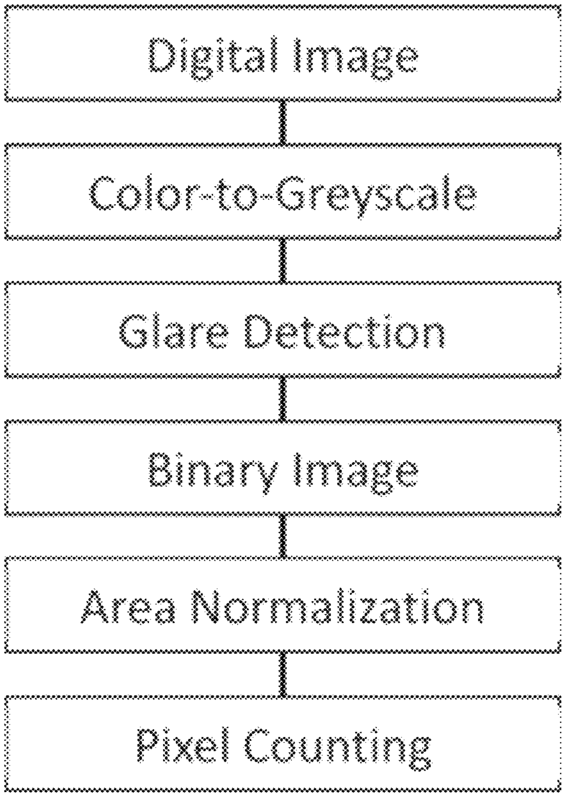
FIG. 2 shows a possible sequence of process steps in the process step of digital image evaluation.

FIG. 2 displays in detail the example digital image processing and result generation. The analysis process starts after digital image recording (step 1) with a color-to-grey-scale-transformation (step 2) based on the single pixels of the digital image data (step 1). If necessary, the digital image is transferred into an RGB-color domain beforehand and the grey-scale transformation is best performed on the RGB-image data. Especially, in the case of a blue color indicator on the test strip the greyscale transformation may greatly increase the reliability and significance of the read-out, compared to routines purely based on evaluation of the color space-data (RGB-data) alone. This is, besides the data reduction, the major advantage of the greyscale transformation. After transformation to greyscale intensity values a checkup-routine for glare detection is performed (step 3), avoiding false process outcomes based on inappropriate digital recording conditions. In the next step (step 4) the greyscale values can be transferred to a binary (black/white) image using an appropriate threshold routine. Pixels comprising greyscale-values above a certain threshold are set to 1 (black), whereas pixels comprising greyscale-values below that threshold are set to 0 (white). In the next step (step 5) an area normalization of the black/white image is performed, wherein also it is checked whether or not the "right" part of the test strip was imaged. The size of the image may be scaled with respect to the size of reference pictures or data omitted in cases where not the indicator area or only a small part thereof was imaged. In the last step (step 6) the black and white pixels are counted and for instance based on the pixel ratio a result is calculated.

Figure 3A:
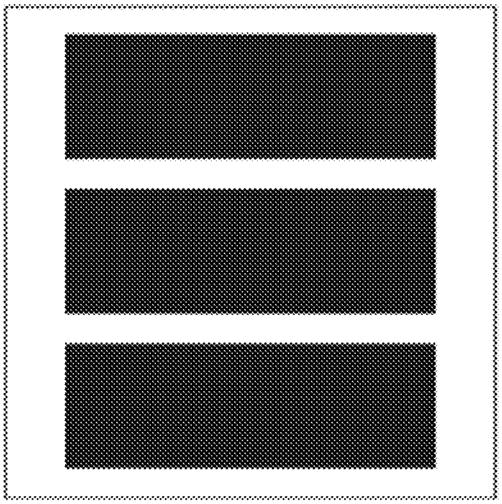
FIG. 3*a* shows one possible test strip design.

FIG. 3*a* displays a schematic drawing of a possible test strip design. The test strip can be rectangular in shape and the test strip area comprising the color indicator can be divided into different areas. This figure exhibits three separated color indicator areas, wherein in between the areas no indicator is present. Such indicator set-up may enhance the significance of the evaluation, because the lines can further be used for image recognition and transformation purposes.

Figure 3B:
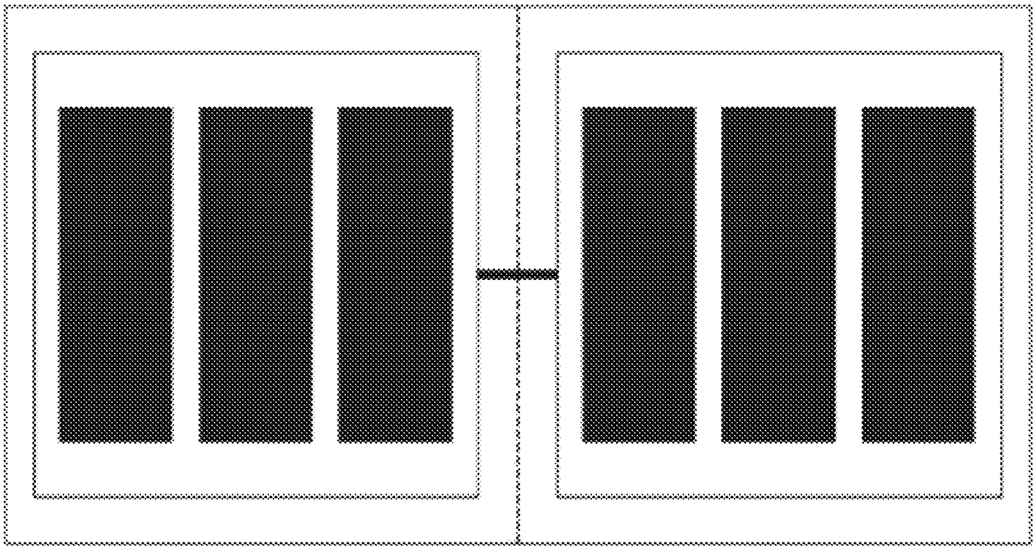
FIG. 3*b* shows another possible test strip design.

FIG. 3*b* depicts a similar test indicator setup as displayed in FIG. 3*a* with the difference, that two test strips are attached together. Therefore, it is for instance possible to monitor the same spot in a washing machine, being subject to a cleaning liquid from two different sides by bending the strip in the middle portion. In addition, it is possible to use the two readouts of the test strips for comparison purposes.

Figure 4A:
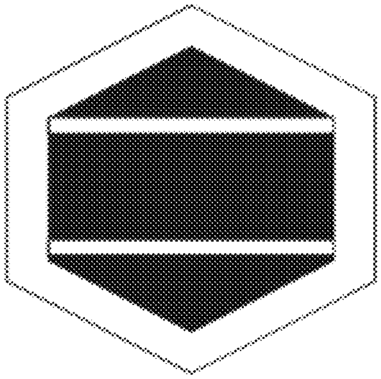
FIG. 4*a* shows one possible test strip design.

FIG. 4*a* displays a test area design, wherein the color indicator is located inside a hexagon. The hexagon may be marked on the test strip by 6 lines of equal length. This set-up may increase the reliability of the area normalization.

Figure 4B:
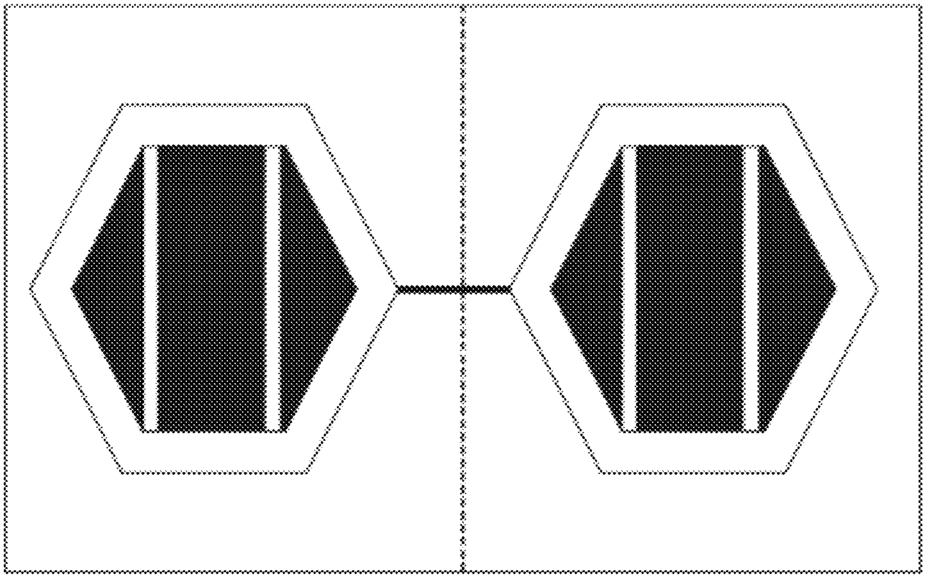
FIG. 4*b* shows another possible test strip design.

FIG. 4*b* displays two attached test strips of the test strip design displayed in FIG. 4*a*. The same advantages apply as described for FIG. 3*b*.

Figure 5A:
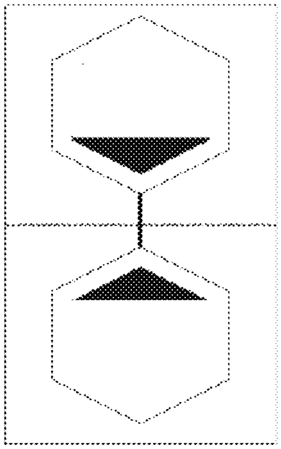
FIG. 5*a* shows one test strip image after a cleaning operation including an image transformation and evaluation process without adaptive thresholding and without luminescence color transformation.
Figure 5B:
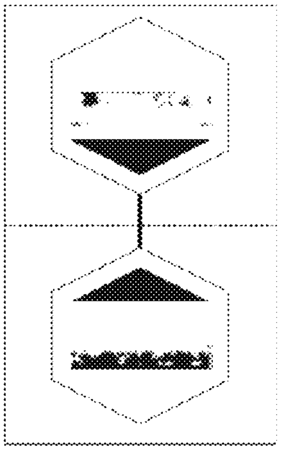
FIG. 5*b* shows one test strip image after a cleaning operation including an image transformation and evaluation process with adaptive thresholding and luminescence color transformation.

FIGS. 5*a* and 5*b* exhibit two images of the same test strip after a washing cycle and after performing the image transformation routine. The original test strip's image comprise three blue indicator areas in each hexagon and after the cleaning process two of the indicator areas are washed off. The middle indicator strip areas exhibit a faded blue color, which could be better discriminated in the FIG. 5*b*. The better discrimination is based on a luminescence color transformation and an adaptive thresholding, whereas for FIG. 5*a* a discarded blue channel and a linear thresholding algorithm are used.

Figure 6:
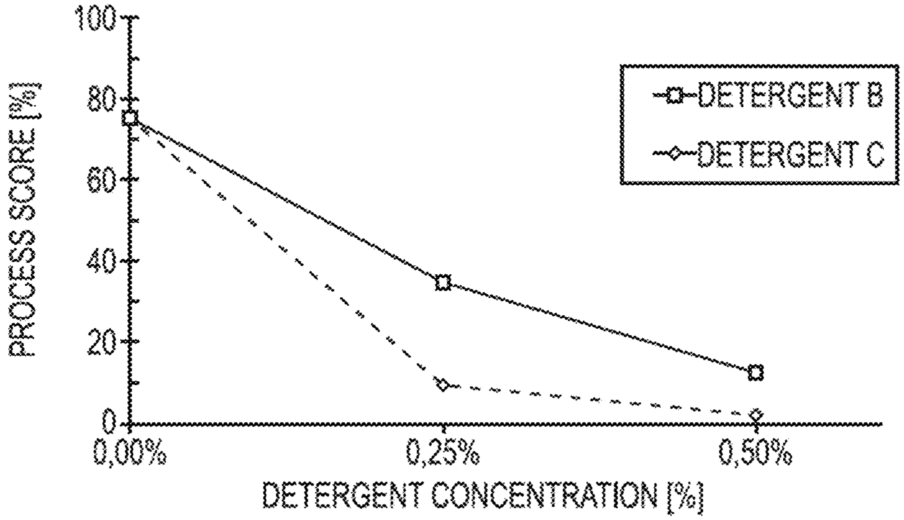
FIG. 6 shows a result of the example process for different detergents and detergent concentrations during a washing cycle.
Figure 7:
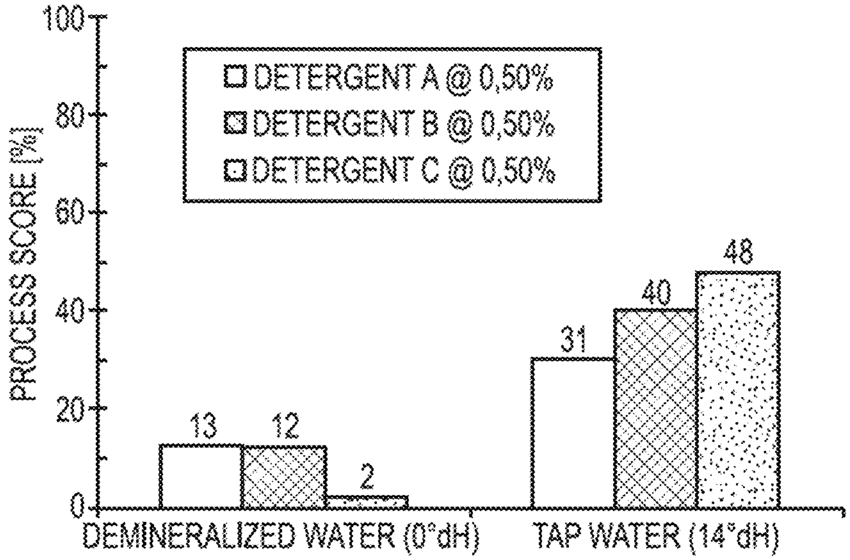
FIG. 7 shows a result of the example process for different water qualities and detergents.

FIGS. 6 and 7 exhibits the results of the example process in the form of a diagram. The testing conditions and the process outcome is discussed in the examples section.

Figure 8:
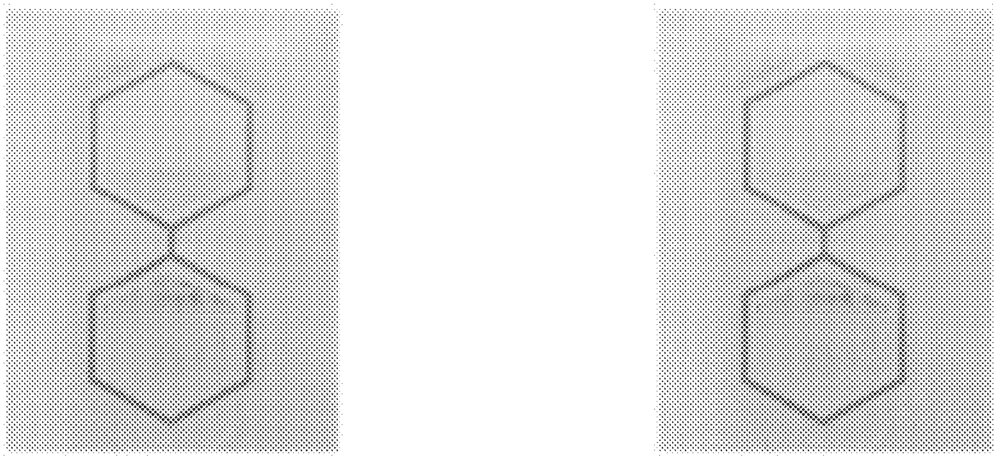
FIG. 8 shows two results of the example process for the same cleaning process and different evaluation routines.

FIG. 8 exhibits a comparison of two evaluation routines for the same cleaning process. Both figures A and B display the result for a cleaning process with a water hardness of 0° dH and a detergent dosage of 0.5%. The left picture (A) is calculated with a discarded blue channel and only a linear threshold algorithm. The overall routine results in a reading of only 3% (given as the ratio of black to white pixels). FIG. 8 B displays the result using a routine according to the disclosure (inter alia including luminescence transformation and adaptive thresholding). Contrary to the other evaluation routine the outcome here is 12%. In addition, the overall standard deviation by monitoring the same process is much smaller by using the example routine.

Figure 9:
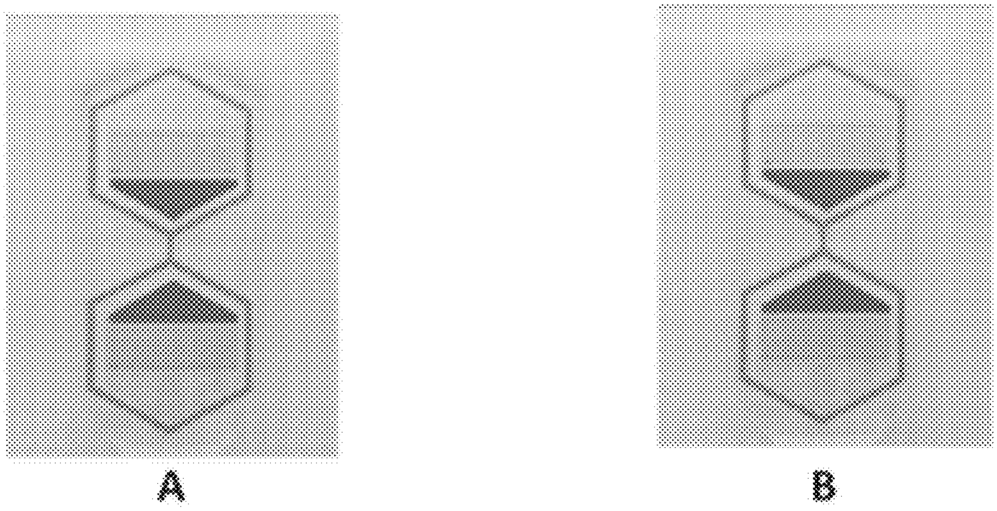
FIG. 9 shows two results of the example process for the same cleaning process and different evaluation routines.

FIG. 9 exhibits a comparison of two evaluation routines for the same cleaning process. Both figures A and B display the result for a cleaning process with a water hardness of 14 and a detergent dosage of 0.5%. The left picture (A) is calculated with a discarded blue channel and only a linear threshold algorithm. The overall routine results in a reading of only 29% (given as the ratio of black to white pixels). FIG. 9 B displays the result using a routine according to the disclosure (inter alia including luminescence transformation and adaptive thresholding). Contrary to the other evaluation routine the outcome here is 46%. In addition, the overall standard deviation by monitoring the same process is much smaller by using the example routine.

EXAMPLES

In order to test the reproducibility of the example process a washing test was monitored using test strips comprising a blue color indicator and a double sided set-up as depicted in FIG. 4.

The test conditions were: deionized water (fully demineralized) 0° dH, machine Miele 8528, cleaning cycle temperature 55° C., cleaning time 10 minutes, detergent concentration 0.50%; detergent A Sekumatic ProClean (mild-alkaline detergent from Ecolab Deutschland GmbH), detergent B MetalClean plus (mild-alkaline detergent from Ecolab Deutschland GmbH), detergent C Thermosept X-tra (enzymatic, mild-alkaline detergent from Schulke & Mayr GmbH).

Example 1

10 washing cycles were performed and the test strips subjected to the example process, i.e. luminescence color transformation of the RGB-image, glare detection in the HSV-domain using a 10 pixel criteria, adaptive thresholding in a 251×251 matrix around the pixel(x,y) and a constant C of 5, image area normalization based on the hexagon area and pixel counting. For the evaluation the ratio of black and white pixel is used. In a further step the result is transformed in a process score, wherein the ratio is scaled by a factor to normalize the obtained ratio in between 0% (fully clean, no indicator left on the strip) and 100% (indicator unchanged by washing cycle).

For the detergent A the following results are obtained 18, 14, 12, 12, 13, 8, 11, 8, 15, 15. This results in an average of 13 and a standard deviation of 3.1.

For the detergent B the following results are obtained 12, 13, 12, 14, 13, 15, 11, 12, 13, 9. This results in an average of 12 and a standard deviation of 1.6.

For the detergent C the following results are obtained 4, 2, 2, 3, 2, 1, 2 (7 measurements only). This results in an average of 2 and a standard deviation of 1.0.

It has been shown that the example process is able to discriminate between different detergents and that according to the standard deviation the routine yields highly reproducible results.

Example 2

The same test set-up as described in example 1 was used and for two detergents (B and C) the concentration was varied between (0 and 0.5%). The result of the example process is depicted in FIG. 6. The overall process is able to clearly discriminate between the different detergents and, in addition, is also able to discriminate between the different detergent concentrations. This result is based on the better accuracy and reproducibility of the transformation and evaluation process. Please note that also the overall washing conditions are monitored by the indicator, because the process score is around 80% without any detergent.

Example 3

Figure 10:
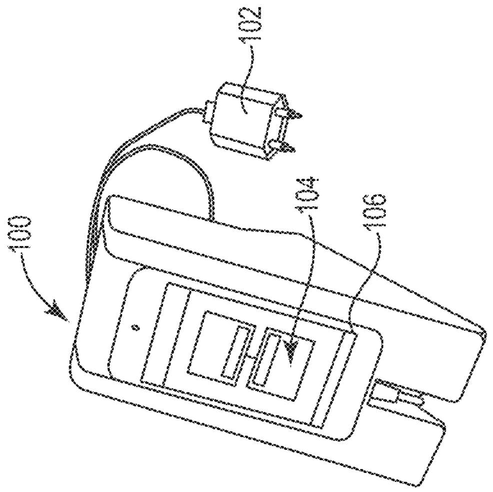
FIG. 10 shows a photograph of a imaging box that may be used for image capture of a chemical test strip using a mobile device.

Based on the same set-up as described for example 1 the influence of the water quality was tested on the outcome of the example process. The results are depicted in FIG. 7. It can clearly be seen that the example process is able to discriminate between the three detergents and, in addition, also further process conditions like the water quality can reliably be monitored Imaging Box FIG. 10 shows a photograph of an example imaging box 100 that may be used for image capture of a chemical test strip using an example mobile device 106. Mobile device 106 includes a power cable 102 and a user interface 104 that displays results of the cleaning assessment.

Figure 11:
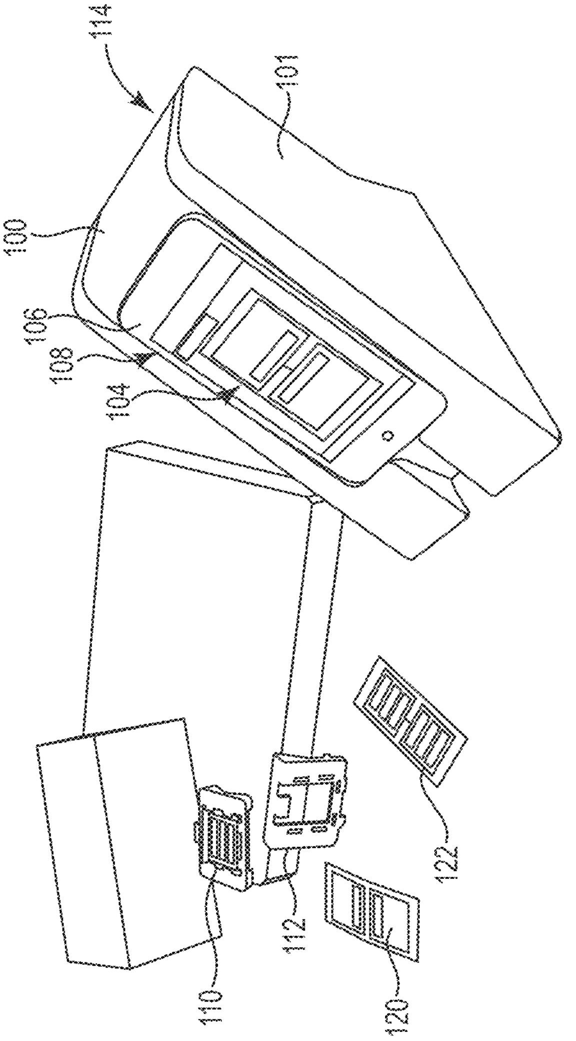
FIG. 11 shows a photograph of an imaging box having a mobile device docked thereto, example chemical test strips and example chemical test strip holders.

FIG. 11 shows a photograph of an example imaging box 100 having an example mobile device 106 docked thereto, example chemical test strips 110, 120, and 122, and example chemical test strip holders 112.

Imaging box 100 includes a housing 101 having a receptacle 108 configured to hold a mobile device 106. Imaging box 100 also includes a test strip slot 114 configured to receive and hold a test strip, such as any of test strips 120 or 122, during image capture. Test strip holders 112 are configured to hold test strips in the cleaning environment during the cleaning process. In use, a test strip is folded in half and placed in test strip holder 112 in a folded configuration as shown with respect to test strip 110 in FIG. 11. After the cleaning process is completed, test strip is removed from the test strip holder 112, unfolded, and placed into the test strip slot 114 for image capture.

Test strip slot 114 is configured to receive and hold an unfolded test strip in a substantially flat position so that the position of test strips is consistent during image capture. In addition, test strip slot 114 is configured to receive and hold an unfolded test strip in a fixed position with respect to a mobile device camera when the mobile device is docked into the imaging box as shown in FIGS. 10 and 11. Receptacle 108 is further configured to receive and hold a properly docked mobile device 106 in a consistent and fixed position relative to the position of the test strip when properly loaded into the test strip slot 114. Mobile device 106 includes a user interface 104 configured to display the results of the cleaning assessment.

Figure 12:
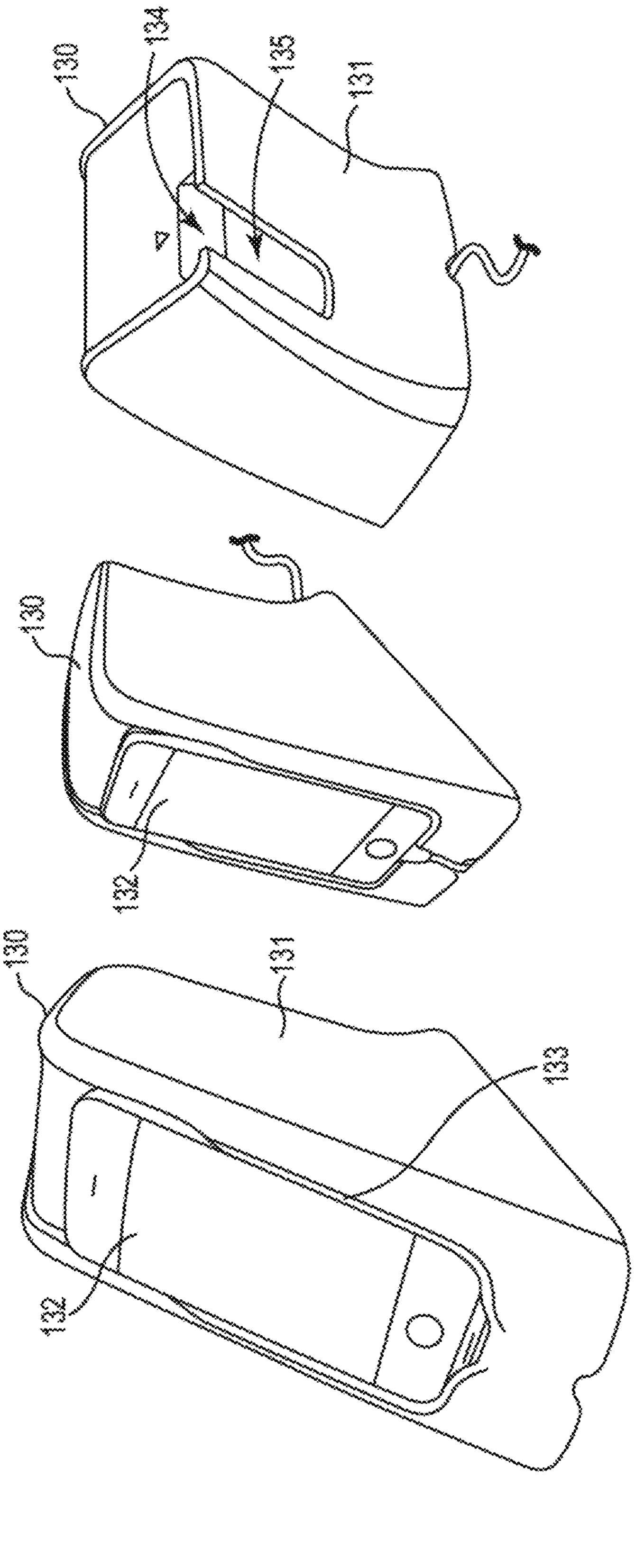
FIG. 12 shows two front perspective and a back perspective views of an example imaging box.

FIG. 12 shows two front perspective views and a back perspective view of an example imaging box 130. Housing 131 of imagining box 130 includes a receptacle 133 configured to receive and hold a mobile device 132 (such as a smart phone or tablet computer) in a consistent and fixed position during image capture. Housing 131 of imaging box 130 further includes a test strip slot 134 configured to receive and hold a test strip and/or test strip holder in a fixed position during image capture. The test strip is loaded into slot 134 with the indicator area facing the interior cavity of housing 131. Housing 131 further includes an imaging aperture 135 through which an image of the indicator area of a test strip loaded into test strip slot 134 may be captured by a mobile device 132 as described herein.

Figure 13:
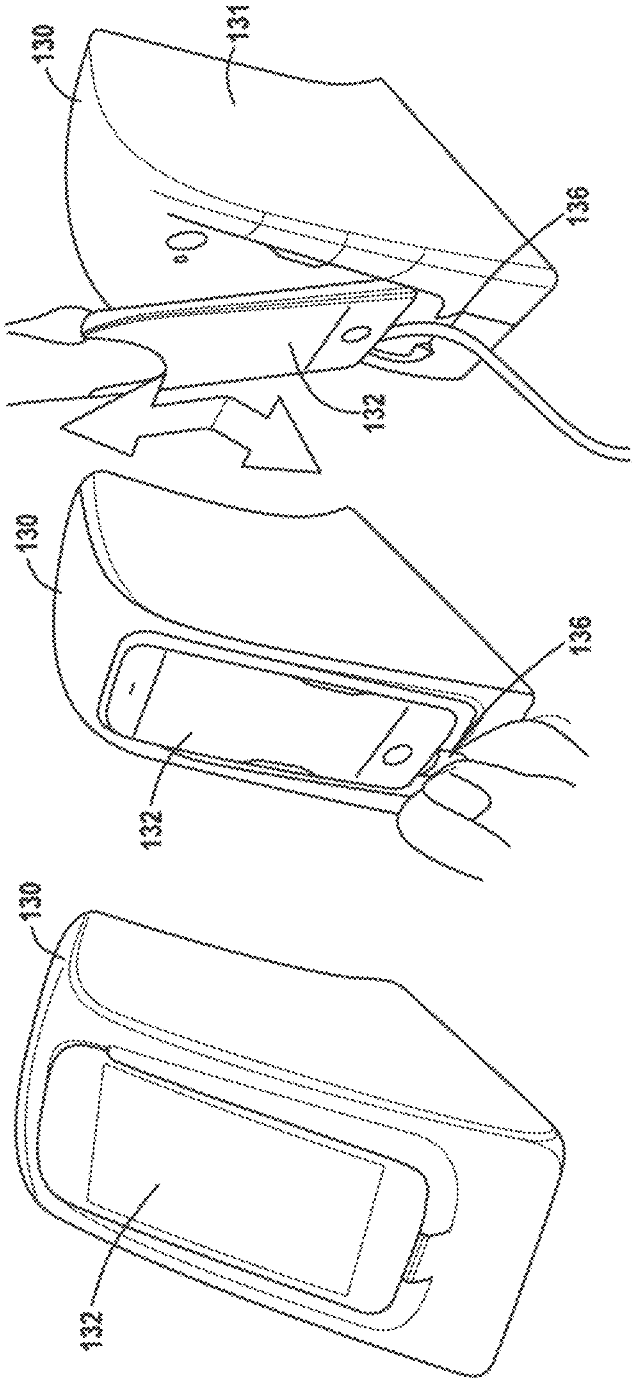
FIG. 13 shows an example imaging box and docking of an example mobile device to the imaging box.

FIG. 13 shows an example imaging box 130 and docking of an example mobile device 132 to the imaging box 130. The housing 131 of imaging box 130 further includes cable management slot 136 sized to receive a power cable of mobile device 132 when mobile device 132 is properly docked onto imagine box 130.

Figure 14:
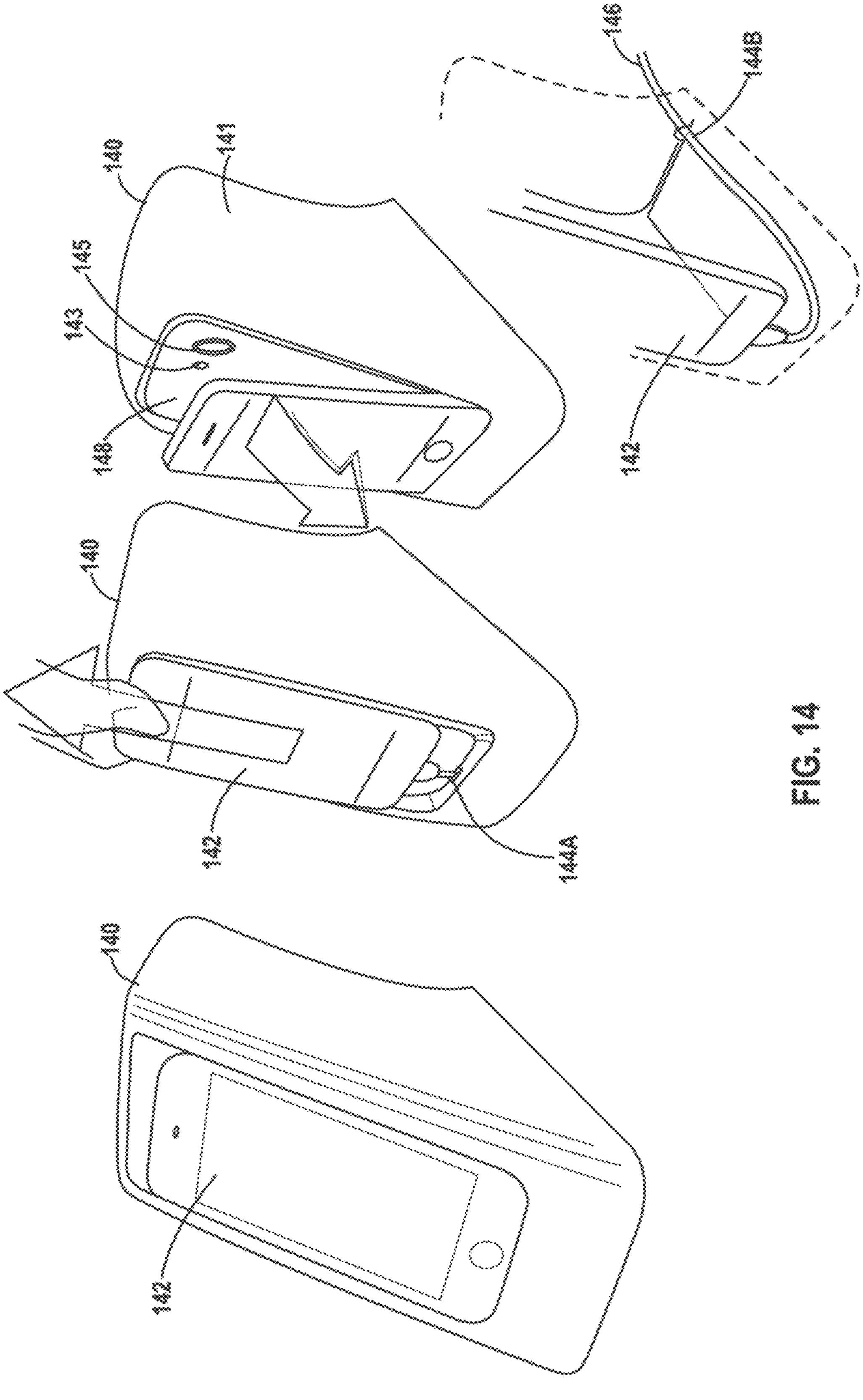
FIG. 14 shows another example imaging box and docking of an example mobile device to the imaging box.

FIG. 14 shows another example imaging box 140 and docking of an example mobile device 142 to the imaging box 140. The housing 141 of imaging box 140 includes cable management apertures 146A and 146B sized to receive a power cable of mobile device 142 when mobile device 142 is properly docked onto imagine box 140. Receptacle 148 of housing 141 also includes a camera aperture 145 and a light source aperture 143. Camera aperture 145 and light source 143 are configured to align with a camera lens and flash, respectively, on a mobile device, such as mobile device 142. If different type of mobile device is used, the camera and/or light source apertures 145, 143 may be located in a different position within receptacle 148. Camera aperture 145 is further configured to align with respect to an imaging aperture on a back surface of housing 141 (see, e.g., FIG. 12) such that an image of the indicator area on a test strip may be captured by the mobile device camera through the camera aperture 145.

Figure 15:
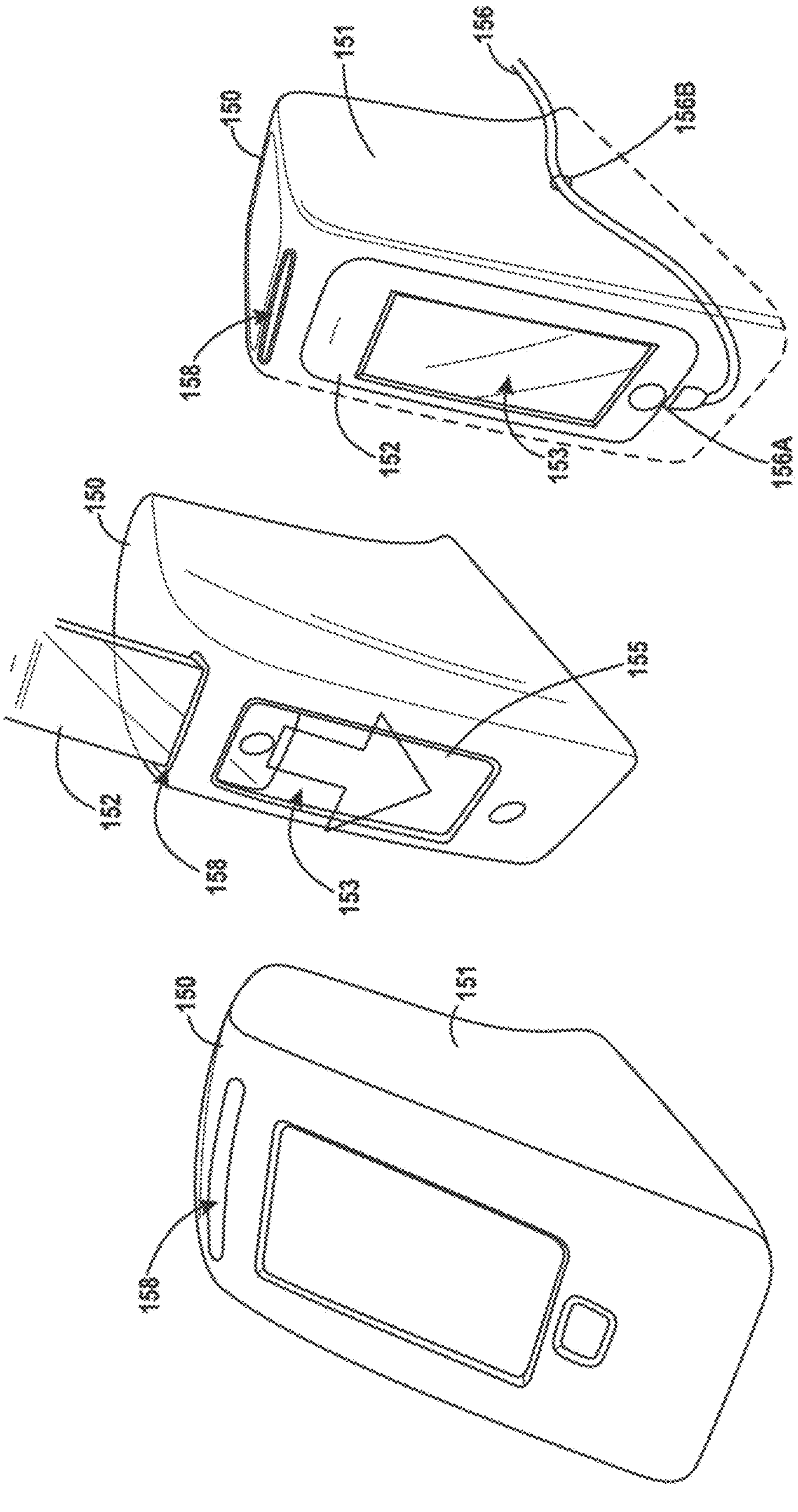
FIG. 15 shows another example imaging box and docking of an example mobile device to the imaging box.

FIG. 15 shows another example imaging box 150 and docking of an example mobile device 152 to the imaging box 150. The housing 151 of imaging box 150 includes cable management apertures 156A and 156B sized to receive a power cable of mobile device 152 when mobile device 152 is properly docked onto imagine box 150. Housing 151 of imaging box 150 includes a slot 158 configured to receive and hold a mobile device 152. Housing 151 further includes a display aperture 155 on the front surface of the housing 151 sized to expose at least the touch screen display portion 153 of mobile device 152 accessible to a user. Although not shown in FIG. 15, the housing 151 also includes a camera aperture 145 and a light source aperture 143 within slot 158 that are configured to align with a camera lens and flash, respectively, on a mobile device, such as mobile device 152.

Figure 16:
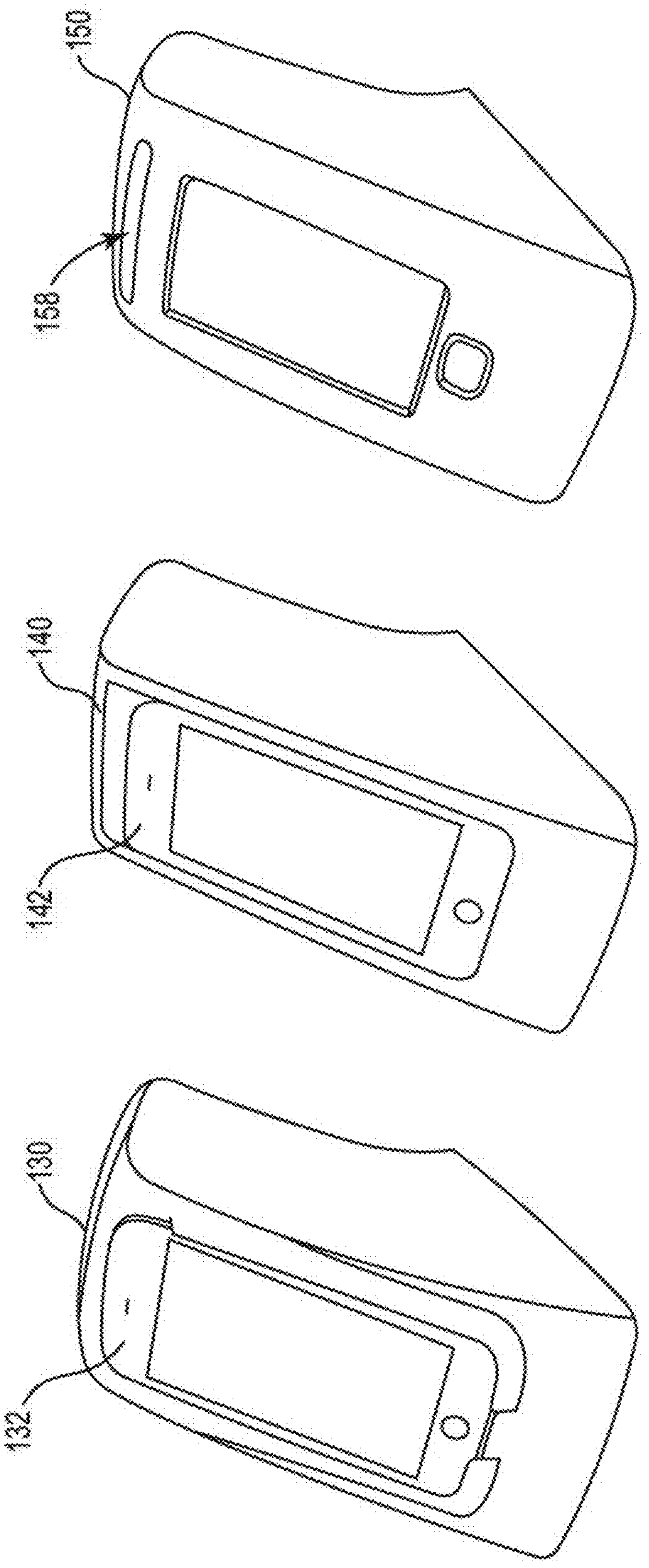
FIG. 16 show front perspective views of an example mobile device docked to the example imaging boxes of FIGS. 13, 14, and 15, respectively.

FIG. 16 show front perspective views of an example mobile devices 132, 142, and 152, docked to the example imaging boxes of FIGS. 13, 14, and 15, respectively.

Figure 17:
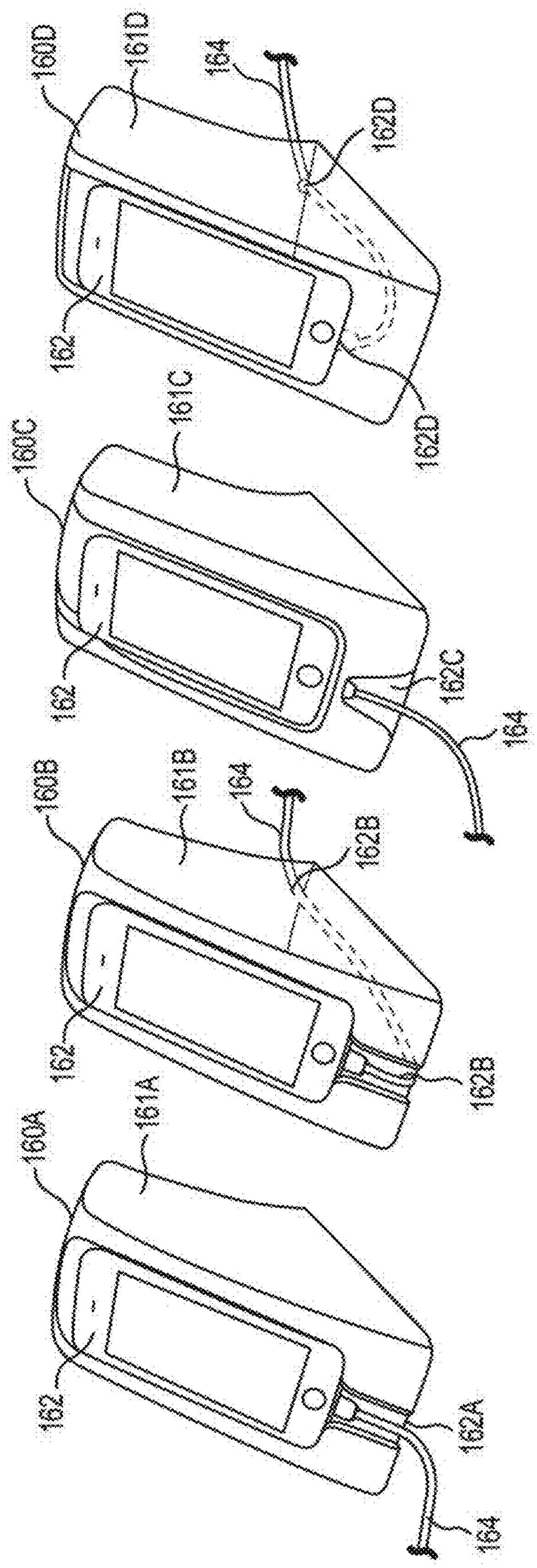
FIG. 17 show front perspective views of an example mobile device docked to additional example imaging boxes, each of which includes a different cable management technique.
Figure 18:
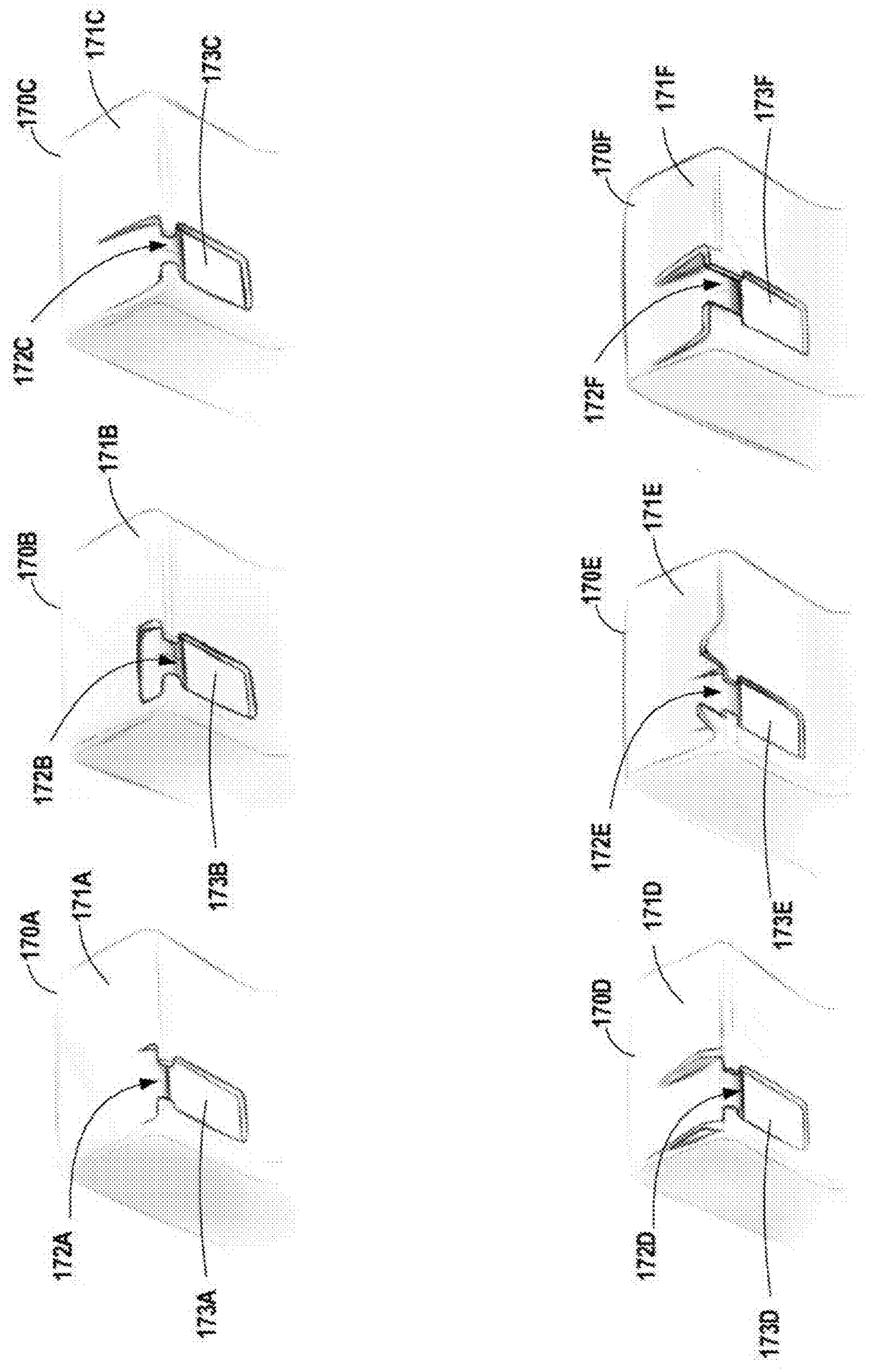
FIG. 18 show views of six different example chemical test strip slots.

FIG. 17 show front perspective views of an example mobile device 162 docked to additional example imaging boxes 160A-160D, each of which includes a different cable management technique. Housing 161A of imaging box 160A, for example, includes a cable slot 162A sized to receive a power cable 164 of a mobile device. Housing 161B of imaging box 160B, for example, includes a cable slot/aperture(s) 162B sized to receive a power cable 164 of a mobile device. Housing 161C of imaging box 160C, for example, includes a cable aperture/slot 162C sized to receive a power cable 164 of a mobile device. Housing 161D of imaging box 160D, for example, includes a cable slot(s) 162D sized to receive a power cable 164 of a mobile device FIG. 18 show views of six different example chemical test strip slots 172A-172F in the housings 171A-171F of example imaging boxes 170A-170F, respectively. Chemical test strips 173A-173F are positioned within chemical test strip slots 172A-172F, respectively, with the indicator area (s) of the test strip 1713A-173F facing the interior cavity of the respective imaging box 170A-170F.

Figure 19:
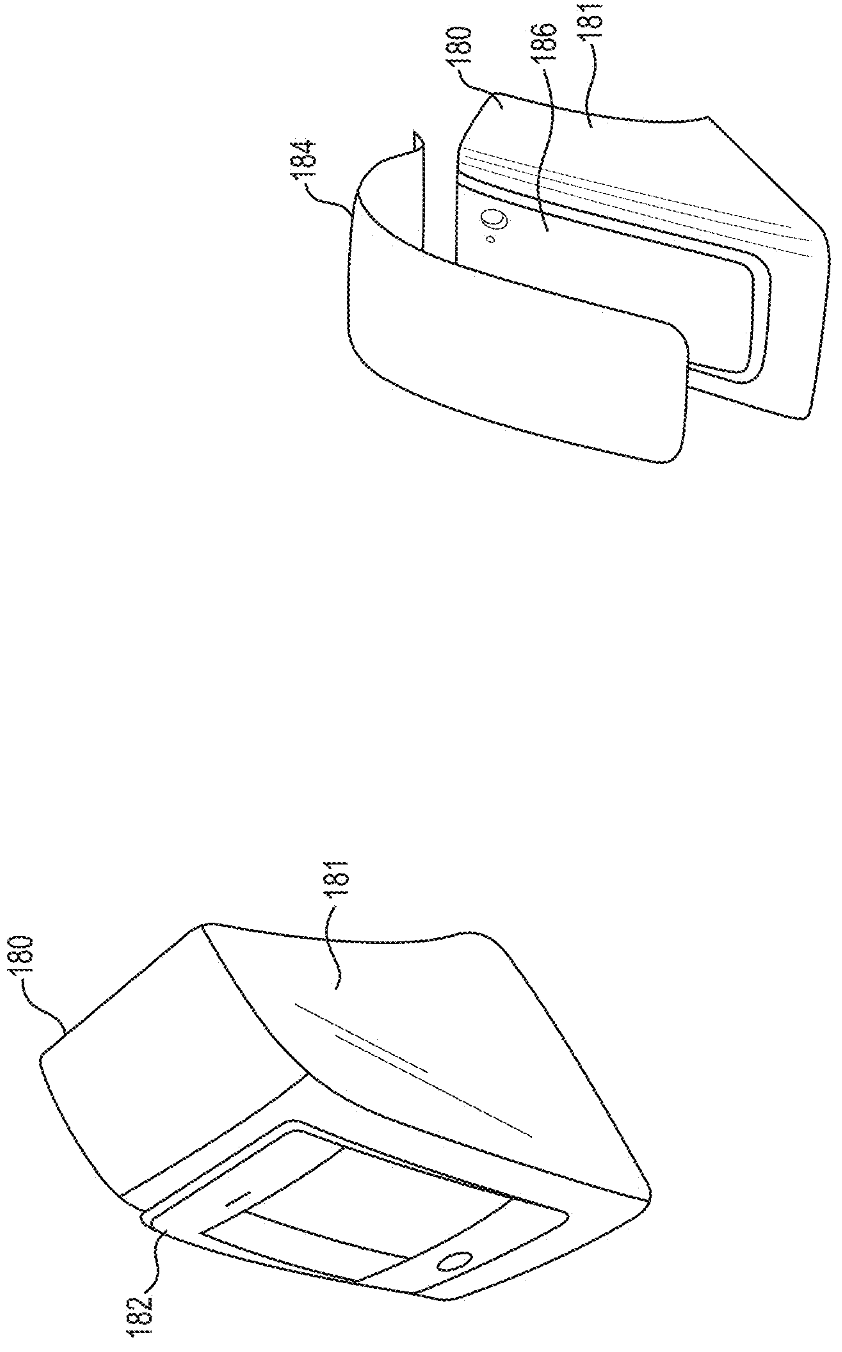
FIG. 19 show perspective views of an example imaging box and an example light covering sticker.

FIG. 19 show perspective views of an example imaging box 180 configured to receive a mobile device 182 and an example light covering sticker 184. In this example, light covering sticker 184 covers the device receiving receptacle 186 and a top surface of housing 181. Light covering sticker prevents light from showing through the housing 181 of imaging box 180 when the flash of mobile device 182 is activated during image capture of the indicator area of a chemical test strip. This may help prevent light coming through housing 181 from affecting the lighting conditions during the image capture process, and thus the quality of the resulting image.

Figure 20:
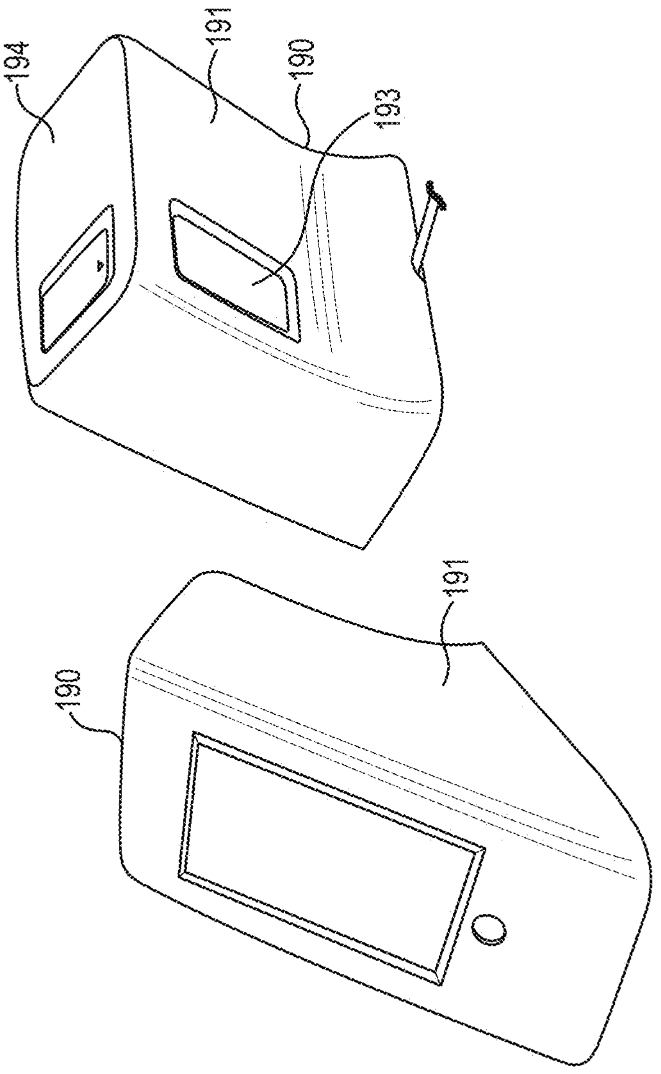
FIG. 20 show perspective views of an example imaging box and another example light covering sticker.

FIG. 20 show perspective views of an example imaging box 190 and another example light covering sticker 194. In this example, light covering sticker 194 covers only the top surface of imaging box 190. Light covering sticker 194 prevents light from showing through the top surface of housing 191 of imaging box 190 when the flash of mobile device 192 is activated during image capture of the indicator area of a chemical test strip 193. This may help prevent light coming through housing 191 from affecting the lighting conditions during the image capture process, and thus the quality of the resulting image.

Figure 21:
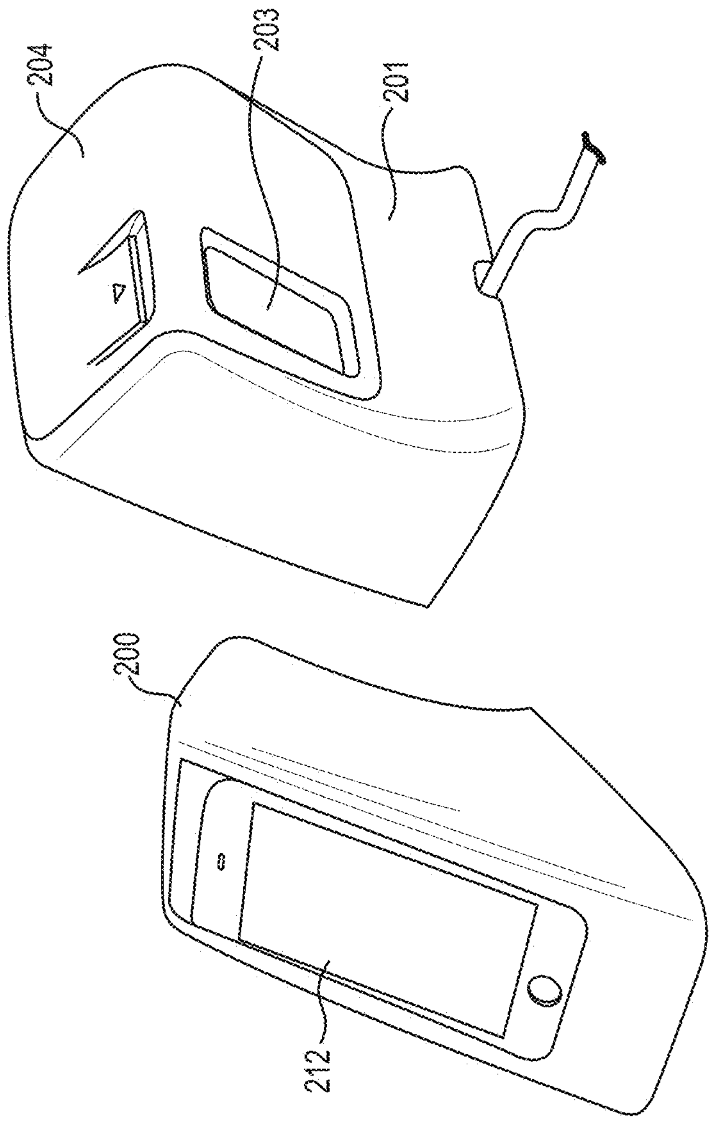
FIG. 21 show perspective views of an example imaging box and another example light covering sticker.

FIG. 21 show perspective views of an example imaging box 200 and another example light covering sticker 204. In this example, light covering sticker 204 covers the top and back surfaces of imaging box 200. Light covering sticker 204 prevents light from showing through the top and back surfaces of housing 201 of imaging box 200 when the flash of mobile device 212 is activated during image capture of the indicator area of a chemical test strip 203. This may help prevent light coming through housing 201 from affecting the lighting conditions during the image capture process, and thus the quality of the resulting image.

Figure 22:
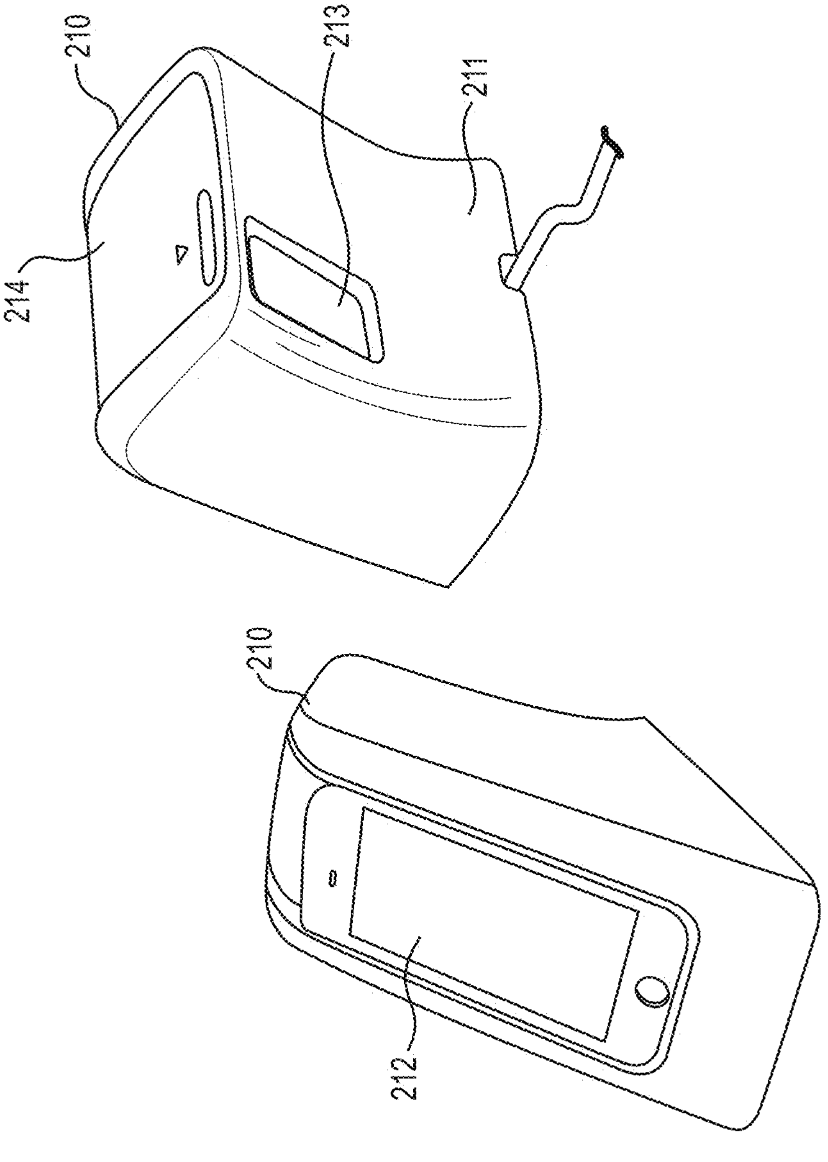
FIG. 22 show perspective views of an example imaging box and another example light covering sticker.

FIG. 22 show perspective views of an example imaging box 210 and another example light covering sticker 214. In this example, light covering sticker 214 covers the device receiving receptacle and a top surface of housing 211. Light covering sticker prevents light from showing through the housing 211 of imaging box 210 when the flash of mobile device 212 is activated during image capture of the indicator area of a chemical test strip. This may help prevent light coming through housing 211 from affecting the lighting conditions during the image capture process, and thus the quality of the resulting image.

Figure 23:
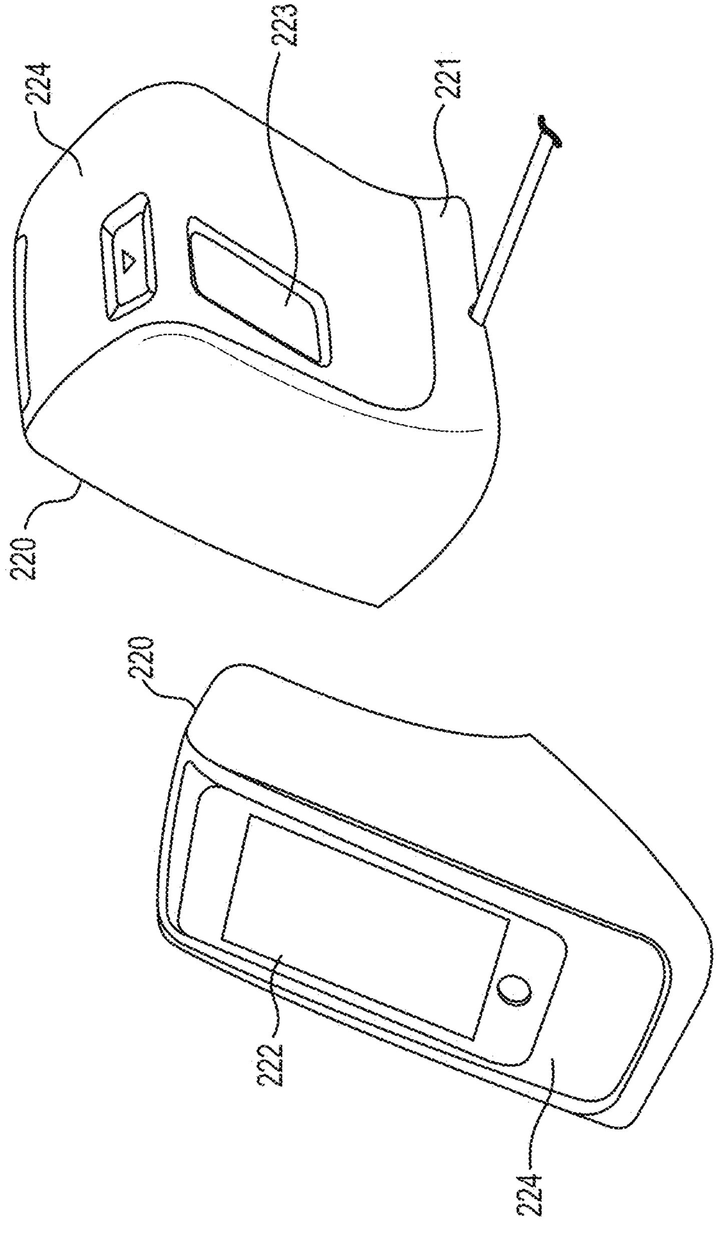
FIG. 23 show perspective views of an example imaging box and another example light covering sticker.

FIG. 23 show perspective views of an example imaging box 220 and another example light covering sticker 224. In this example, light covering sticker 224 covers the device receiving receptacle, a top surface of housing 221, and a back surface of housing 221. Light covering sticker prevents light from showing through the front, top and back surfaces of housing 221 of imaging box 220 when the flash of mobile device 222 is activated during image capture of the indicator area of a chemical test strip. This may help prevent light coming through housing 221 from affecting the lighting conditions during the image capture process, and thus the quality of the resulting image.

Figure 24:
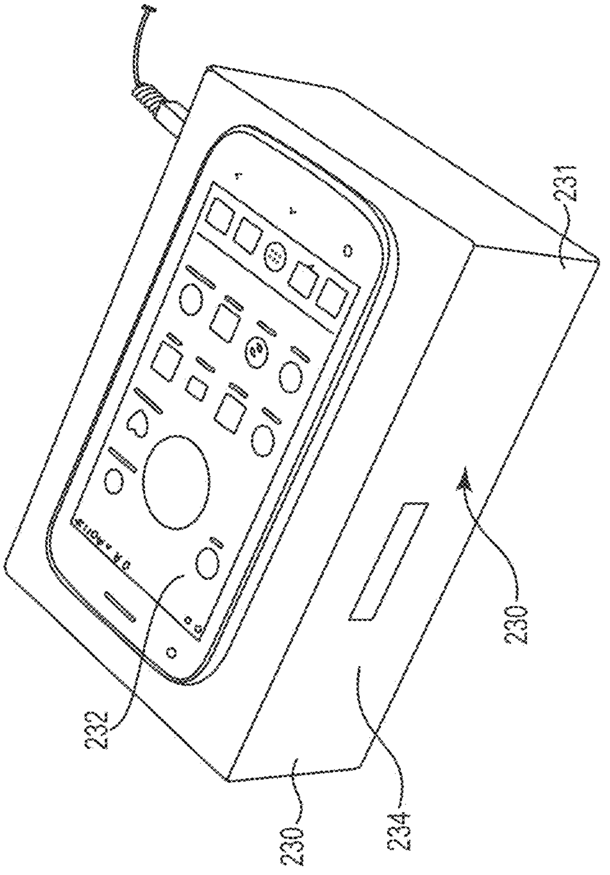
FIG. 24 show perspective views of an example imaging box and another example light covering sticker.

FIG. 24 is a photograph of another example imaging box 230 having a housing 231 forming a cavity 236, an integrated light source 234 inside the cavity 236 of the imaging box 230, and an example mobile device 232 docked thereto.

Figure 25:
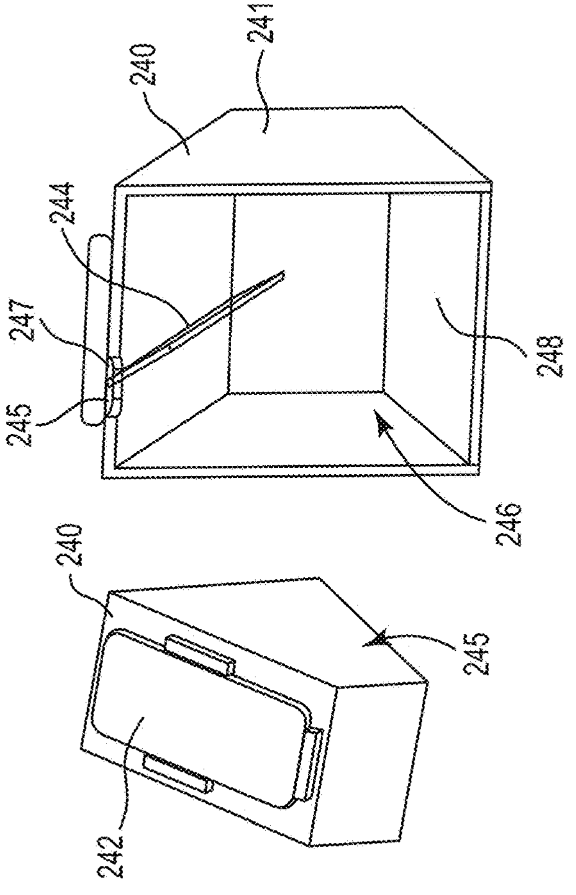
FIG. 25 shows a perspective and a bottom cross-sectional view of an imaging box having a substantially square cross-section and including a substantially flat diffuser rib.

FIG. 25 shows a perspective and a cross-sectional view of an imaging box 240 including a housing 241 having a substantially square cross-section and including a substantially flat diffuser rib 244 in the interior cavity of housing 241. Housing 241 includes a slanted top surface and sidewalls 245 forming an open base portion through which the interior cavity 246 of imaging box 240 may be accessed. Imaging box 240 is configured to receive a mobile device 242 on slanted top surface of the housing 241. A camera aperture 245 and a flash aperture 247 are configured to align with a camera lens and a flash of mobile device 242. Diffuser rib 244 serves to scatter and/or diffusely reflect the relatively more concentrated light directed into the cavity 246 from the camera flash, thus helping to prevent glare or artifacts in the test strip image due to unsuitable or unfavorable light-conditions, e.g. obtained under too much light or with undesirable light reflections.

Figure 26:
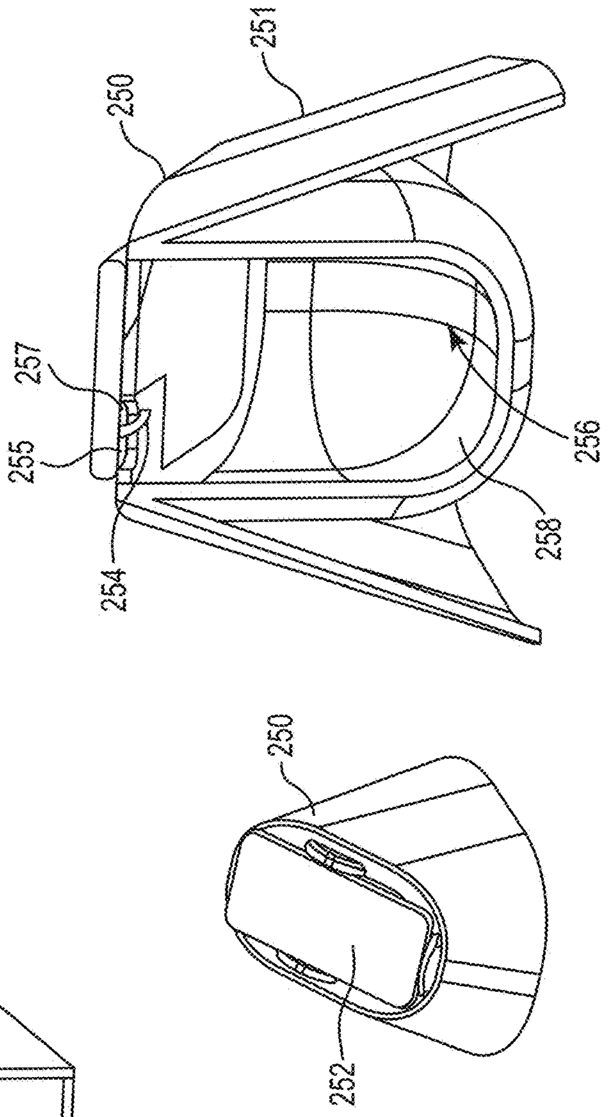
FIG. 26 shows a perspective and a bottom cross-sectional view of an imaging box having interior rounded edges and including a curved diffuser rib.

FIG. 26 shows a perspective and a cross-sectional view of an imaging box 250 an associated mobile device 252. Imaging box 250 includes a housing 251 and an interior cavity 256 formed by interior rounded sidewalls 258. Housing further includes a camera aperture 255 and a flash aperture 257. Housing 251 further includes including a curved diffuser rib 254 positioned proximate to the flash aperture on the interior surface of cavity 258. Curved diffuser rib 254 serves to scatter and/or diffusely reflect the relatively more concentrated light directed into the cavity 256 from the camera flash. The curved shape of diffuser rib 254 may help to diffusely reflect the incident light more uniformly around the cavity 256. In addition, curved interior surfaces 258 may further help to diffusely reflect or scatter the incident light to help prevent glare, bright spots, or artifacts in the captured image.

Figure 27:
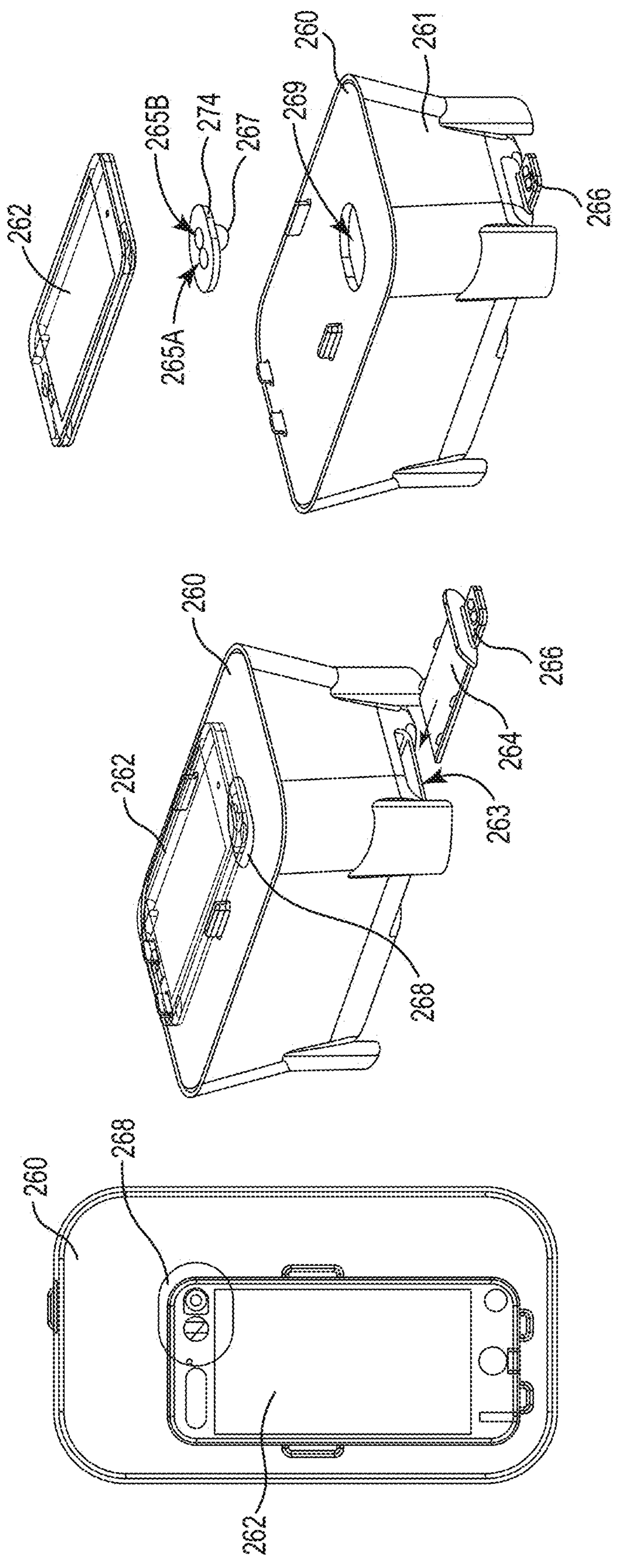
FIG. 27 shows a top view of an example imaging box with an example mobile device docked thereto, a side perspective view of the example imaging box showing a test strip in a test strip slot holder being inserted into a test strip slot, and an exploded view of the imaging box showing a removable diffuser insert.

FIG. 27 shows a top view of an example imaging box 260 with an example mobile device 262 docked thereto, a side perspective view of the example imaging box 260 showing a test strip 264 in a test strip slot holder 266 being inserted into a test strip slot 263, and an exploded view of the imaging box 260 showing a removable diffuser insert 268. A top surface of housing 261 includes an insert aperture 269 sized to receive the removable diffuser insert 268. Removable diffuser insert 268 includes a camera aperture 265A, a flash aperture 265B, and a diffusing rib 267.

Figure 28:
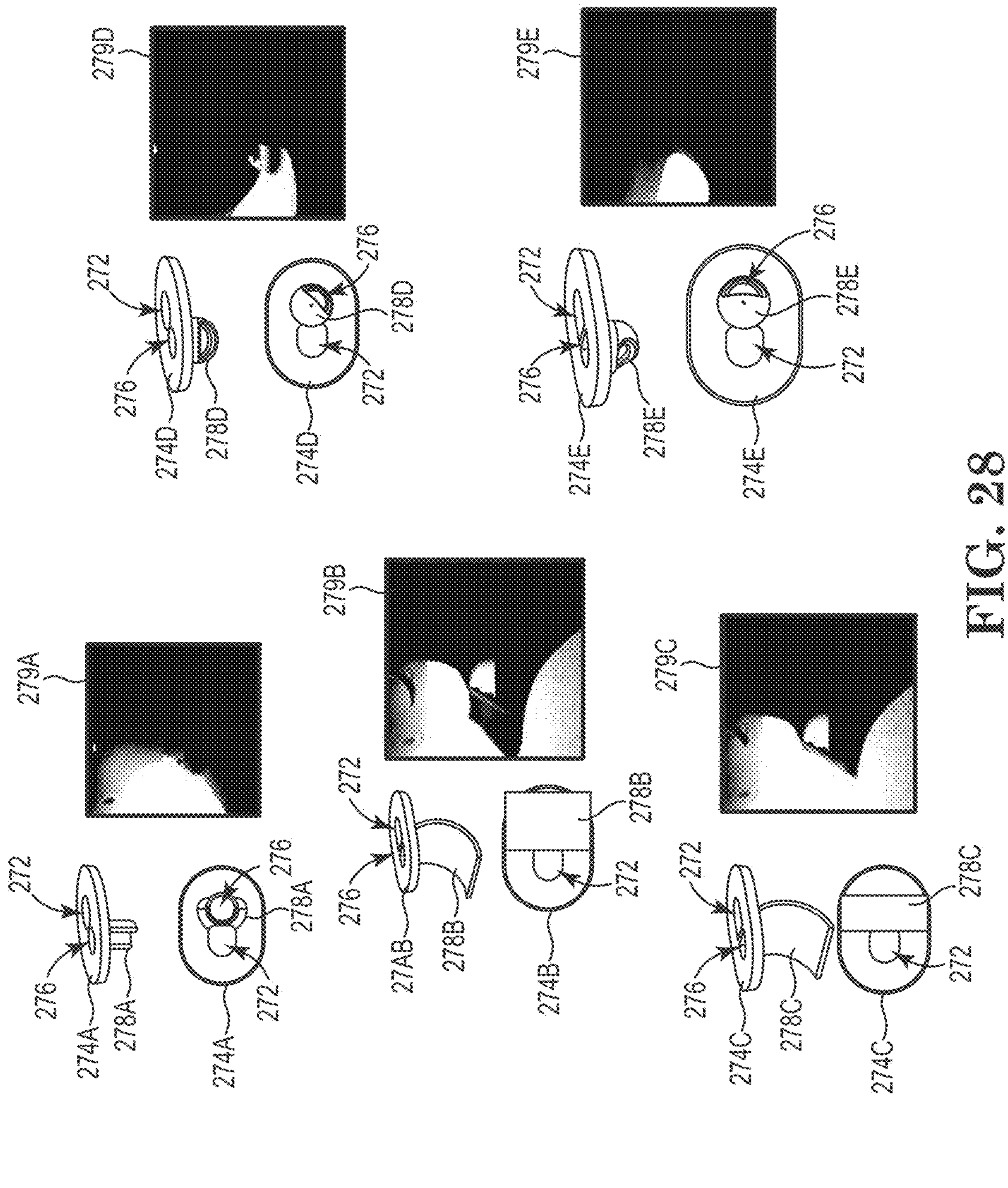
FIG. 28 shows five different imaging box diffusers; a half cylinder diffuser, a large arc diffuser, a small arc diffuser, a dome 45-degree diffuser, and a dome perpendicular diffuser.

FIG. 28 shows five different imaging box diffuser inserts 274A-274E with differently shaped diffusing ribs: a half cylinder diffuser 278A, a large arc diffuser 278B, a small arc diffuser 278C, a dome 45-degree diffuser 278D, and a dome perpendicular diffuser 278E, respectively. Each diffuser insert 274A-274E includes a camera aperture 272 and a flash aperture 276. The diffuser ribs 278A-278E are positioned proximate to flash apertures 276 on the respective diffuser insert 274A-274E. The different shape(s) of diffuser ribs 278A-278E serve to diffusely reflect or scatter light incident into an interior cavity of an imaging box from a flash of a mobile device in such a way as to reduce or eliminate glare, artifacts, or bright spots in images of one or more test strips taken with a mobile device docked with the imaging box. FIG. 28 also shows photographs of the interiors 279A-279E of a light box using the respective diffuser inserts 274A-274E.

Figure 29:
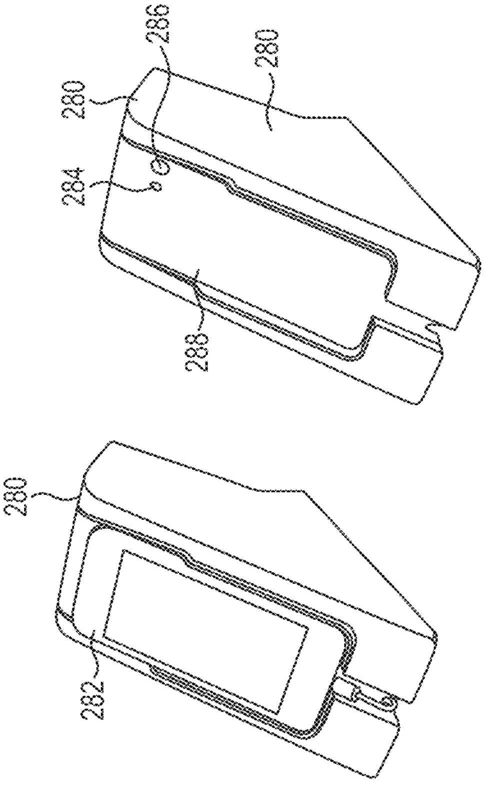
FIG. 29 shows an example imaging box and an example mobile device docked thereto, and an example imaging device along and showing a camera aperture and a flash aperture in the imaging box housing configured to correspond to the position of a mobile device camera lens and a mobile device flash.

FIG. 29 shows an example imaging box 280 and an example mobile device 282 docked thereto, and an example imaging box 280 alone and showing a camera aperture 286 and a flash aperture 284 in the imaging box housing 281 configured to correspond to the position of a mobile device camera lens and a mobile device flash.

Figure 30:
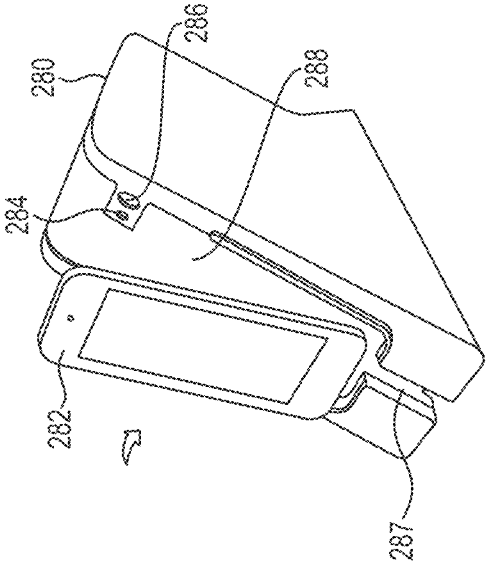
FIG. 30 shows an example imaging box showing the docking process for an example mobile device.

FIG. 30 shows an example imaging box 280 showing the docking process for an example mobile device 282. Imagine box 280 includes a housing 281 having a receptacle 288 configured to receive a mobile device 282. Housing 281 further includes cable slot 287 sized to receive a power cable of mobile device 282. Housing 281 further includes camera aperture 286 and flash aperture 284 configured to correspond to the position of a mobile device camera lens and a mobile device flash, respectively.

Figure 31:
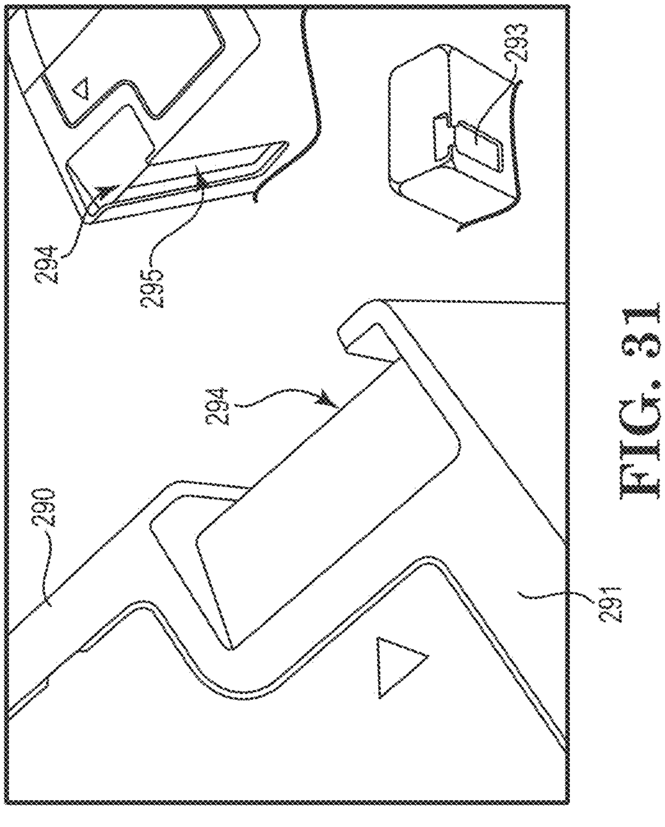
FIG. 31 shows an example test strip slot for an example imaging box.

FIG. 31 shows an example test strip slot 294 in a housing 291 of an example imaging box 290. Test strip slot 294 is sized to receive a test strip 293 with the test strip indicator facing the interior cavity of the housing 291 during the test strip image capture process as described herein. Housing further includes an imaging aperture 295 aligned with test strip slot 294 such that an image of the indicator area of the test strip 293 may be captured by the mobile device camera through the camera aperture.

Figure 32:
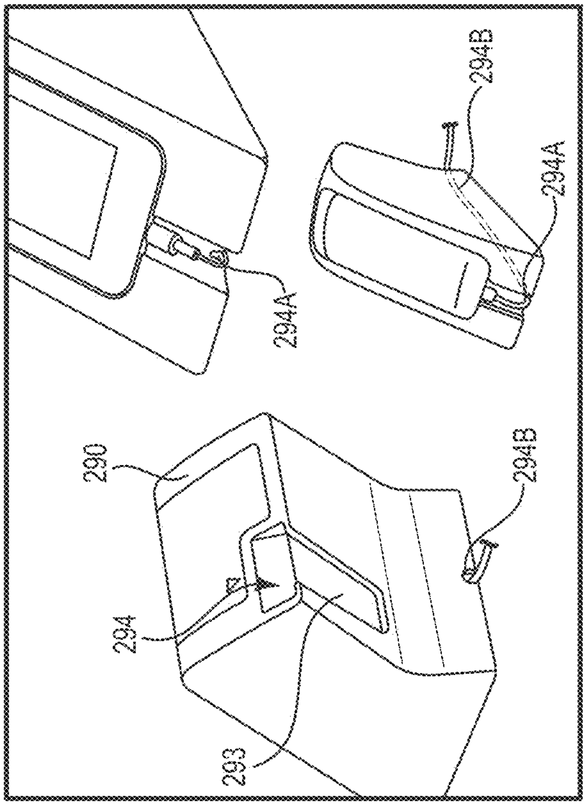
FIG. 32 shows an example of cable management for an example imaging box.

FIG. 32 shows an example of cable management apertures 294A and 294B for an example imaging box 290. FIG. 32 also shows a back view of imaging box 290 in which a test strip 293 is viewable in a test strip slot 294.

Figure 33:
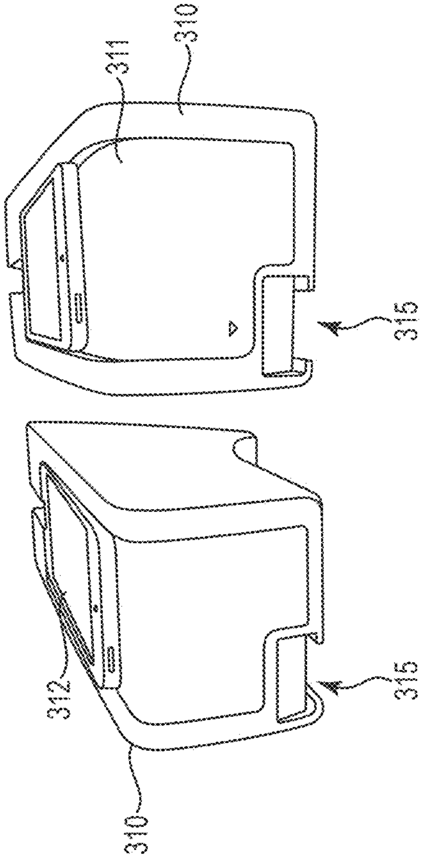
FIG. 33 shows an example test strip slot for an example imaging box.

FIG. 33 shows an example test strip slot 315 in a housing 311 of an example imaging box 310.

Figure 34:
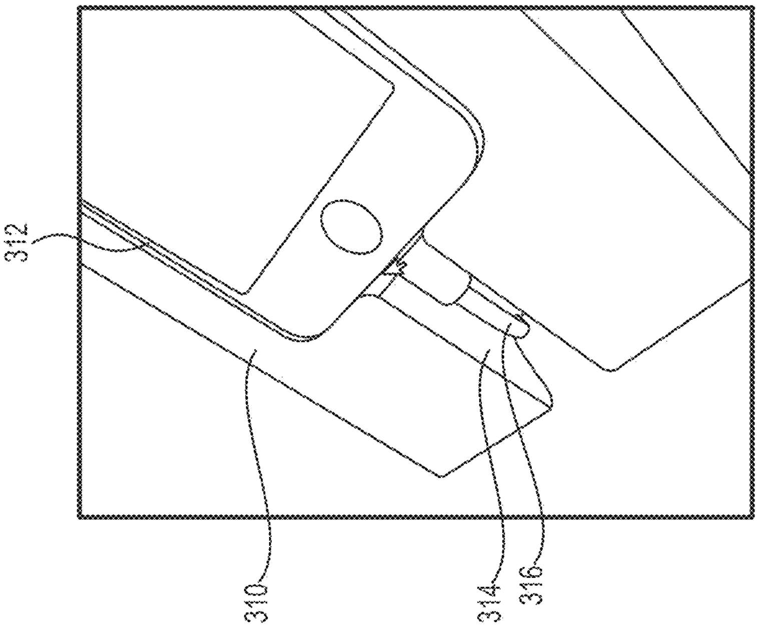
FIG. 34 shows an example of cable management for an example imaging box.

FIG. 34 shows an example of cable management slot 314 in a housing 311 of an example imaging box 310. The slot 314 is sized to receive a power cable 314 of a mobile device 312.

Figure 35:
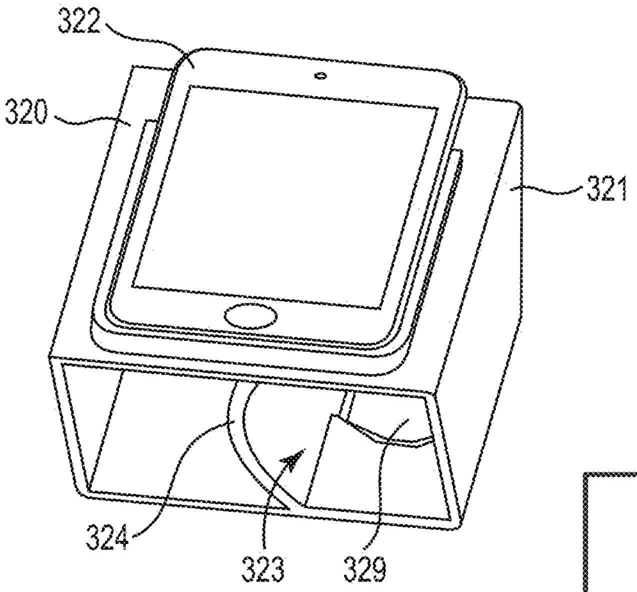
FIG. 35 shows a bottom view of an example imaging box showing the interior of a test strip slot and an interior housing dividing rib.

FIG. 35 shows a bottom cross-sectional perspective view of an example imaging box 320 and a mobile device 322. Imaging box 320 includes a housing 321 defining an interior cavity 326 in which a test strip 329 is positioned for image capture in a test strip slot 328. The interior walls of housing 312 include an interior dividing rib 324. Dividing rib 324 serves to make the interior cavity 323 in which the imaging takes place smaller (as opposed to the entire interior cavity of the housing).

Figure 36:
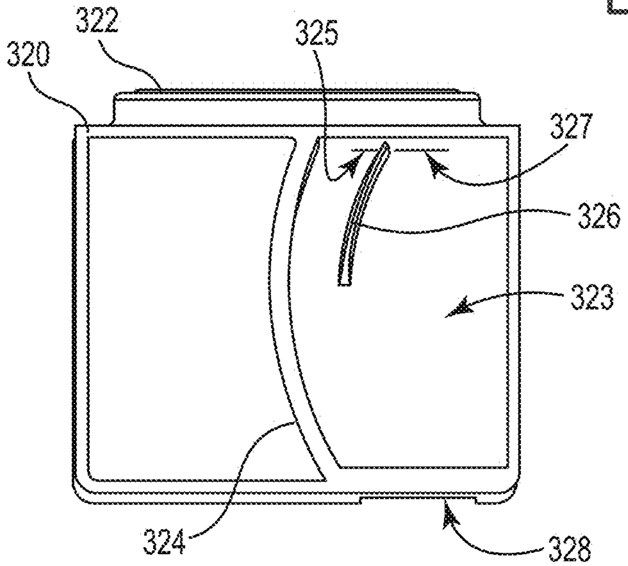
FIG. 36 shows a cross-sectional view of an example imaging box showing a curved diffuser rib and an interior housing dividing rib.

FIG. 36 shows a cross-sectional view of an example imaging box 320 showing a curved diffuser rib 326 positioned proximate to camera aperture 327 and an interior housing dividing rib 324. Dividing rib 324 is curved to help scatter and/or diffusely reflect light incident through flash aperture 325, thus helping to reduce glare, artifacts and/or bright spots in any images captured using imaging box 320.

Figure 37:
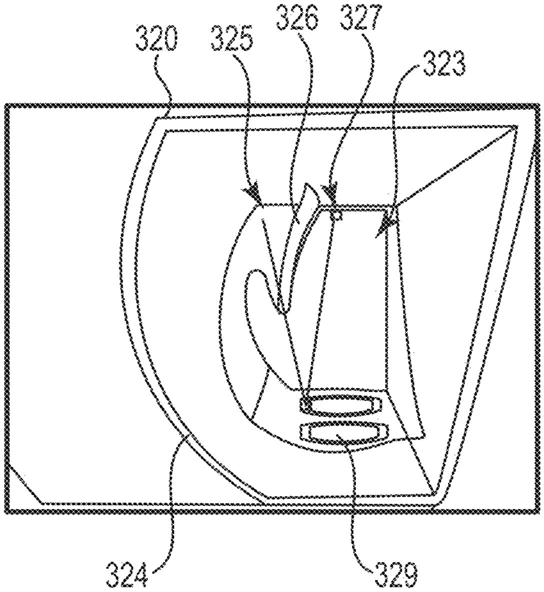
FIG. 37 shows a cross-sectional view of an example imaging box having a chemical test strip inserted therein for image capture, and showing an example curved diffuser rib and an interior housing dividing rib.

FIG. 37 shows a cross-sectional view of an example imaging box 320 having a chemical test strip 329 inserted therein for image capture, and showing an example curved diffuser rib 326 and an interior housing dividing rib 324. FIG. 37 further shows an example light ray entering the interior cavity of imaging box 380 through flash aperture 325, incident upon test strip 329, and exiting through camera aperture 327. Light rays directed as shown in FIG. 37 will pass diffuser rib 325, but any light rays incident at a higher angle of incidence (with respect to diffuser rib 325) will be reflected by diffuser rib 325 and experience additional reflections around the interior of imaging box 380 before being incident upon test strip 329, thus helping to reduce glare, artifacts and/or bright spots in any images captured using imaging box 320.

Figure 38:
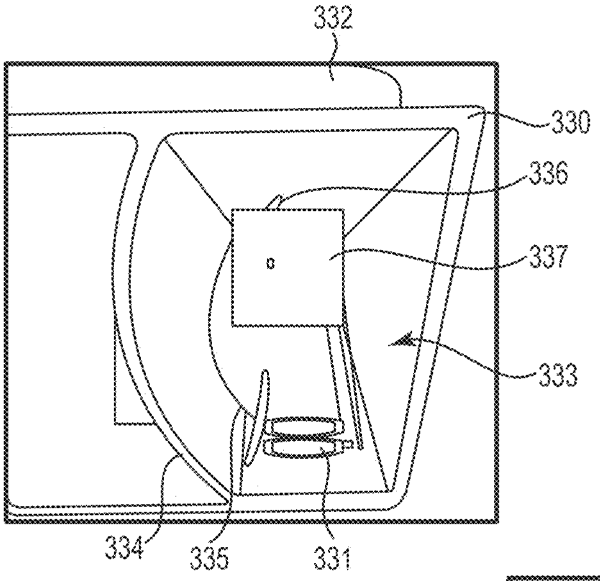
FIG. 38 shows a cross-sectional view of an example imaging box having a chemical test strip inserted therein for image capture, and showing two diffuser ribs and an interior housing dividing rib.

FIG. 38 shows a cross-sectional view of an example imaging box 330 having a chemical test strip 331 inserted therein for image capture, and showing two diffuser ribs 335, 336 and an interior housing dividing rib 334. Imaging box 330 further includes an interior cavity 333. Imaging box 330 further includes a transverse reflective surface 337 that may additionally serve to diffusely reflect and/or scatter light incident into cavity 333.

Figure 39:
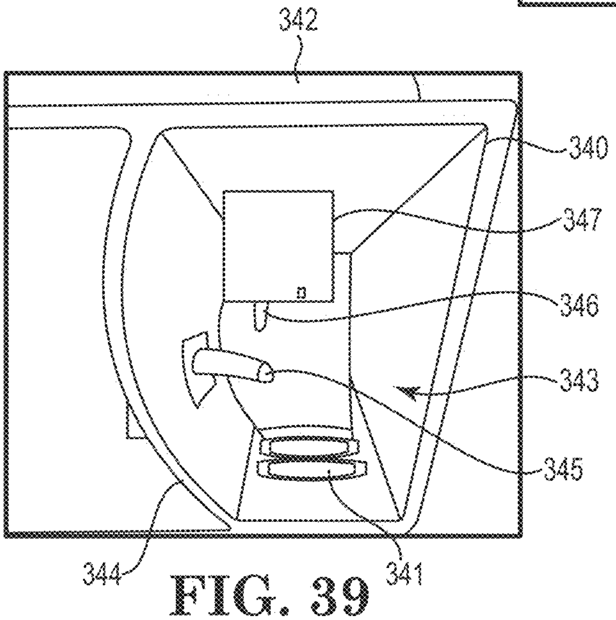
FIG. 39 shows a cross-sectional view of an example imaging box having a chemical test strip inserted therein for image capture, and showing two diffuser ribs and an interior housing dividing rib.

FIG. 39 shows a cross-sectional view of an example imaging box 340 having a chemical test strip 341 inserted therein for image capture, and showing two diffuser ribs 345, 346, and an interior housing dividing rib 344. Imaging box 340 further includes an interior cavity 343. Imaging box 340 further includes a transverse reflective surface 347 that may additionally serve to diffusely reflect and/or scatter light incident into cavity 343.

Figure 40:
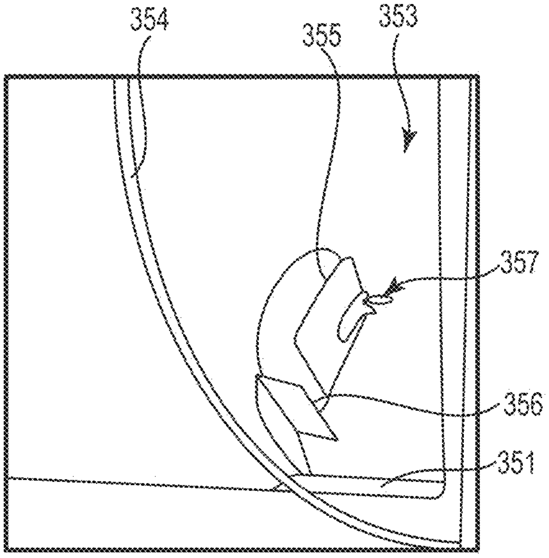
FIG. 40 shows a cross-sectional view of an example imaging box having two diffuser ribs and an interior housing dividing rib.

FIG. 40 shows a cross-sectional view of an example imaging box 350 having two diffuser ribs 355, 356, and an interior housing dividing rib 354. Imaging box 350 also includes an interior cavity 357 and a camera aperture 357.

Cleaning Performance Assessment System

Figure 41:
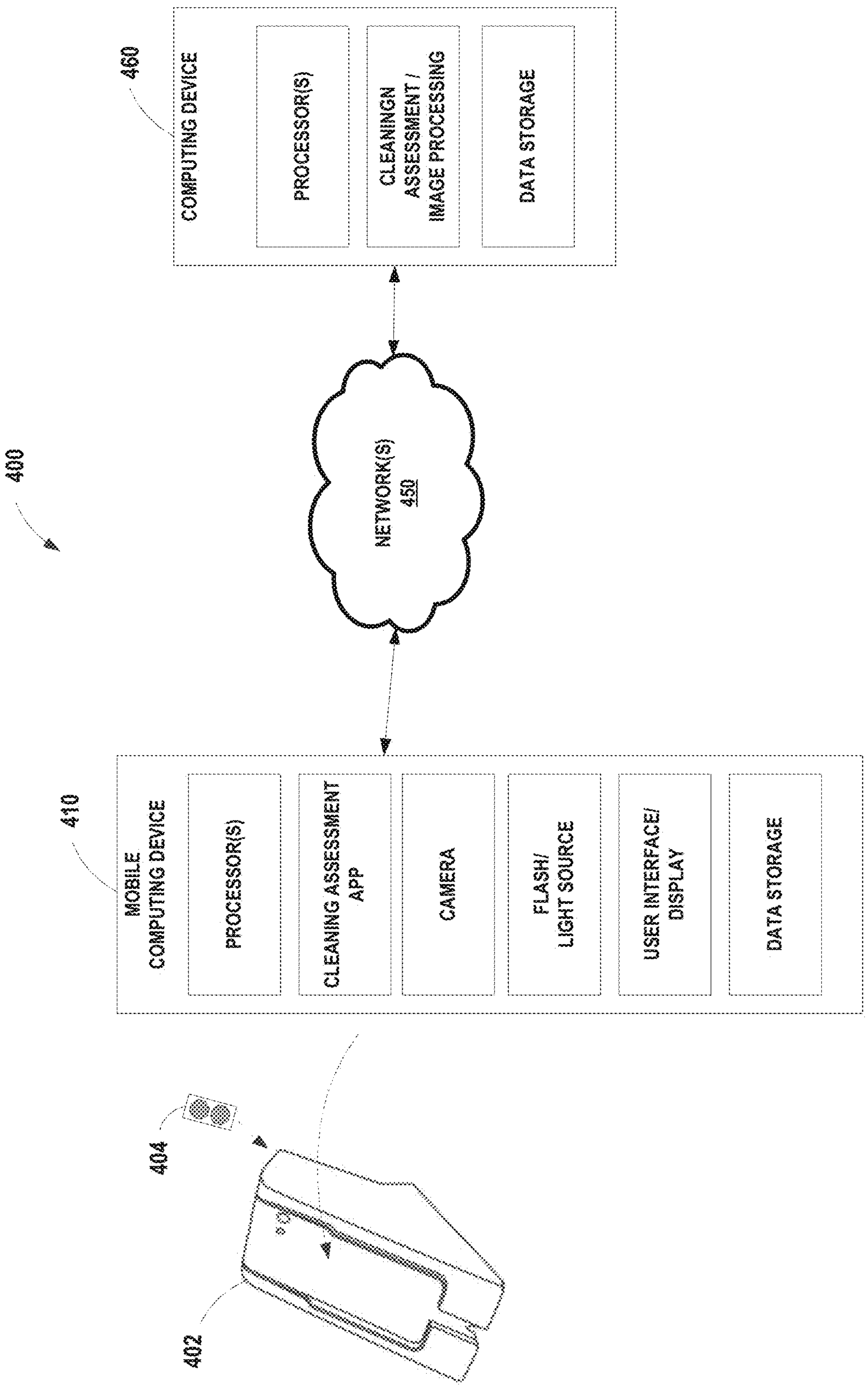
FIG. 41 shows a block diagram of a system 200 for assessing the performance of a cleaning process. The system includes an imaging box 202 for use in an image capture procedure for the performance assessment of a cleaning process. The system 200 further includes a cleaning assessment application configured to be executed on a mobile computing device 210.

FIG. 41 shows a block diagram of a system 400 for assessing the performance of a cleaning process. The system includes an imaging box 402 for use in an image capture procedure for the performance assessment of a cleaning process. The system 400 further includes a cleaning assessment application configured to be executed on a mobile computing device 410.

The system 400 further includes a computing device 460 configured to receive and evaluate the digital image of the chemical test strip and generate an assessment of the performance of the cleaning process.

The imaging box 402 includes a housing defined by a front surface and a back surface and forming an interior cavity when the housing is placed on a substantially flat surface, the front surface having a receptacle configured to receive a mobile device 410. The front surface further including at least one camera aperture configured to correspond to the position of a camera lens of the mobile device when the mobile device is received in the receptacle. The back surface includes a test strip slot configured to receive and hold a chemical test strip comprising a carrier and an indicator means in a substantially flat position. The back surface further includes a test strip aperture configured to correspond to the position of a chemical test strip 404 when received into the test strip slot, such that an image of the chemical test strip may be captured by the camera of the mobile device when the chemical test strip 404 is inserted into the test strip slot such that the indicator means is facing the interior cavity of the housing.

The mobile device 410 includes one or more processors, a cleaning assessment application configured to be executed on the one or more processors, a camera, a flash/light source, a user interface/display, and a memory/data storage.

The cleaning application is configured to receive and display the assessment of the performance of the cleaning process on the user interface of the mobile computing device 410.

The cleaning assessment application may be further configured to guide a user through a chemical test strip image capture procedure. The steps of the procedure may be displayed on the graphical user interface/display of the mobile device 410.

The computing device 460 may be located remotely with respect to the mobile device. In that case, the mobile device 410 and the computing device 460 may communicate through one or more networks 450, or through any suitable form of data communication (e.g., wired or wireless network, short-range wireless communication such as Near Field Communication or Bluetooth, etc.). The networks and/or the communication may be wired or wireless. The networks may include, for example, one or more local area network(s) (LAN), wide area network(s) (WAN), virtual private network(s) (VPN), a wireless or Wi-Fi network, a cellular network, a satellite communication network, or any other means of electronic communication.

The computing device 460 may be configured to evaluate the digital image of the chemical test strip according to the image processing techniques described herein. For example, cleaning assessment/image processing instructions on computing device 460 may include instructions that cause the one or more processors to execute the image processing techniques described herein.

In accordance with one or more aspects of this disclosure, the term "or" may be interrupted as "and/or" where context does not dictate otherwise. Additionally, while phrases such as "one or more" or "at least one" or the like may have been used in some instances but not others, those instances where such language was not used may be interpreted to have such a meaning implied where context does not dictate otherwise.

In one or more examples, the functions described may be implemented in hardware, software, firmware, or any combination thereof. If implemented in software, the functions may be stored on or transmitted over, as one or more instructions or code, a computer-readable device or medium and executed by a hardware-based processing unit.

Computer-readable media may include computer-readable storage media, which corresponds to a tangible medium such as data storage media, or communication media including any medium that facilitates transfer of a computer program from one place to another, e.g., according to a communication protocol. In this manner, computer-readable media generally may correspond to non-transitory tangible computer-readable storage media. Data storage media may be any available media that can be accessed by one or more computers or one or more processors to retrieve instructions, code and/or data structures for implementation of the techniques described in this disclosure. A computer program product may include a computer-readable medium.

By way of example, and not limitation, such computer-readable storage media can comprise RAM, ROM, EEPROM, CD-ROM or other optical disk storage, magnetic disk storage, or other magnetic storage devices, flash memory, or any other medium that can be used to store desired program code in the form of instructions or data structures and that can be accessed by a computer. Also, any connection is properly termed a computer-readable medium. For example, if instructions are transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio, and microwave are included in the definition of medium. It should be understood, however, that computer-readable storage media and data storage media do not include connections, carrier waves, signals, or other transient media, but are instead directed to non-transient, tangible storage media. Disk and disc, as used, includes compact disc (CD), laser disc, optical disc, digital versatile disc (DVD), floppy disk and Blu-ray disc, where disks usually reproduce data magnetically, while discs reproduce data optically with lasers. Combinations of the above should also be included within the scope of computer-readable media.

Instructions may be executed by one or more processors, such as one or more digital signal processors (DSPs), general purpose microprocessors, application specific integrated circuits (ASICs), field programmable logic arrays (FPGAs), or other equivalent integrated or discrete logic circuitry. Accordingly, the term "processor," as used may refer to any of the foregoing structure or any other structure suitable for implementation of the techniques described. In addition, in some aspects, the functionality described may be provided within dedicated hardware and/or software modules. Also, the techniques could be fully implemented in one or more circuits or logic elements.

The techniques of this disclosure may be implemented in a wide variety of devices or apparatuses, including a wireless handset, an integrated circuit (IC) or a set of ICs (e.g., a chip set). Various components, modules, or units are described in this disclosure to emphasize functional aspects of devices configured to perform the disclosed techniques, but do not necessarily require realization by different hardware units. Rather, as described above, various units may be combined in a hardware unit or provided by a collection of interoperating hardware units, including one or more processors as described above, in conjunction with suitable software and/or firmware.

EXAMPLES

Example 1. Process for the performance assessment of cleaning operations at least comprising the steps of:

a) exposing at least one chemical test strip comprising a carrier and an indicator means, wherein the indicator means comprises at least in a defined surface area a color indicator, to the chemical environment of a cleaning operation;

b) recording with an image device the data of at least one digital color image of the test strip after the cleaning operation; and c) quantitative evaluation of the digital image data, characterized in that the quantitative evaluation of the digital color image data in step c) at least comprises the steps c1) to c5):

c1) color-to-greyscale image data transformation;

c2) glare detection;

c3) greyscale- to binary image data transformation;

c4) image pixel-area normalization; and step c5) pixel-counting, wherein the number of black and white pixels of the test strip image data after the cleaning process are counted and the counting result is compared to the quantitative evaluation result of the test strip prior to the cleaning process.

Example 2. Process according to example 1, wherein in step c1) the color-to-greyscale transformation is a luminescence RGB-color-to-greyscale data transformation according to the following equation $$Y = 0.299R + 0.587G + 0.114B,$$

wherein Y is the resulting greyscale- and R, G, B are the RGB-values of the color pixel, respectively.

Example 3. Process according of any one of examples 1 or 2, wherein the greyscale- to binary image data transformation in step c3) is achieved by an adaptive threshold transformation.

Example 4. Process according to example 3, wherein the adaptive threshold transformation in step c3) is achieved by the following mathematical function $$dst(x, y) = \begin{cases} 255 & \text{if } src(x, y) > T(x, y) \\ 0 & \text{otherwise} \end{cases}$$

wherein dst(x,y) is the binary result of the transformation, src(x,y) the greyscale-value of the pixel(x,y) and T(x,y) an individual pixel threshold value, wherein the individual pixel threshold value is calculated from the mean greyscale-value of the pixel neighborhood minus a constant C.

Example 5. Process according to example 4, wherein the mean greyscale-value of the pixel neighborhood is calculated from a 251×251 matrix around the pixel(x,y) and the constant C is 5.

Example 6. Process according of any one of examples 1-5, wherein the glare detection in step c2) at least comprises the transformation of the digital color image data into a HSV-color domain and performing a glare detection based on the V(x,y)-value of individual pixels or pixel areas.

Example 7. Process according to example 6, wherein image spots larger than 10×10 pixels are excluded from further evaluation if all pixels within the spot comprise V(x,y)-values larger than 95% of the maximum V-value of the digital image.

Example 8. Process according of any one of examples 1-7, wherein the image pixel-area normalization in step c4) is based on an image recognition process of the binary image obtained in step c3), wherein the chemical test strip comprises additional lines surrounding the indicator area and only the pixel area between the lines contribute to the quantitative evaluation of the digital image.

Example 9. Process according to example 8, wherein the image pixel-area normalization in step c4) is based on an image recognition process of the binary image obtained in step c3), wherein the chemical test strip comprises additional lines of equal length connected in the form of a geometrical body and only the pixel area within the geometrical body contribute to the quantitative evaluation of the digital image.

Example 10. Process according of any one of examples 1-9, wherein a mathematical transformation of the number of black and white pixel of the test strip image data obtained in step c5) is performed at least comprising the calculation of a black to white pixel ratio and, in a step d), a further grouping of the mathematical transformation result in quality classes is carried out.

Example 11. Process according to example 10, wherein based on the result of the grouping in step d) an action plan is selected.

Example 12. System for the performance assessment of cleaning operations, the system comprises at least:

a chemical test strip having a reactive zone, the reactive zone is operable to change color as a function of a cleaning process;

a chemical test strip receptacle forming an imaging chamber to provide uniformity in lighting and distance between the imaging device and the chemical test strip during imaging of the reactive zone;

an imaging device capable of creating a digital image of the reactive zone of the chemical test strip after the reactive zone has been exposed to the cleaning process;

image analyzing software adapted to count a number of black and white pixels of the digital image of the reactive zone of the chemical test strip after the reactive zone has been exposed to the cleaning process, and compare the counted number of black and white pixels to a quantitative evaluation result of the test strip prior to the cleaning process.

Example 13. The system according to example 12, wherein the test strip comprises at least two separated reactive zones of the same chemical composition.

Example 14. The system according to example 12 or 13, wherein the test strip comprises at least three separated reactive zones of the same or different chemical composition, wherein the surface area ratio of reactive zone to total surface area of the test strip is larger or equal 0.5 and smaller or equal to 0.9.

Example 15. The system according to any one of examples 12 to 14, wherein the test strip comprises additional lines in the form of a geometrical body, wherein the body is selected from the group consisting of parallelogram, hexagon or circle, and the surface area ratio of reactive zone to total surface area within the geometrical body is larger or equal 0.7 and smaller or equal to 0.95.

Example 16. A computer-readable storage medium encoded with instructions that, when executed, cause one or more processors of a computing device to perform operations comprising:

a) exposing at least one chemical test strip comprising a carrier and an indicator means, wherein the indicator means comprises at least in a defined surface area a color indicator, to the chemical environment of a cleaning operation;

b) recording with an image device the data of at least one digital color image of the test strip after the cleaning operation; and c) quantitative evaluation of the digital image data, characterized in that the quantitative evaluation of the digital color image data in step c) at least comprises the steps c1) to c5):

c1) color-to-greyscale image data transformation;

c2) glare detection;

c3) greyscale- to binary image data transformation;

c4) image pixel-area normalization; and step c5) pixel-counting, wherein the number of black and white pixels of the test strip image data after the cleaning process are counted and the counting result is compared to the quantitative evaluation result of the test strip prior to the cleaning process.

Example 17. An imaging box for use in an image capture procedure for the performance assessment of cleaning operations, comprising:

a housing defined by a front surface and a back surface and forming an interior cavity when the housing is placed on a substantially flat surface, the front surface having a receptacle configured to receive a mobile device, the front surface further including at least one camera aperture configured to correspond to the position of a camera lens of the mobile device when the mobile device is received in the receptacle, the back surface including a test strip slot configured to receive and hold a chemical test strip comprising a carrier and an indicator means in a substantially flat position, the back surface further including a test strip aperture configured to correspond to the position of a chemical test strip when received into the test strip slot, such that an image of the chemical test strip may be captured by the camera of the mobile device when the chemical test strip is inserted into the test strip slot such that the indicator means is facing the interior cavity of the housing.

Example 18. The imaging box of example 17, wherein the front surface of the housing further includes a flash aperture configured to correspond to the position of a light emitting flash of the mobile device when the mobile device is received in the receptacle.

Example 19. The imaging box of example 18 further including at least one diffusing rib positioned within the interior cavity of the housing to diffuse light emitted from the flash of the mobile device.

Example 20. The imaging box of example 17 further comprising a light source positioned within the interior cavity of the housing.

Example 21. The imaging box of example 17 further comprising a cord management slot in the front surface of the housing configured to receive a charging cable of the mobile device.

Example 22. The imaging box of example 17 further comprising a light covering sticker sized to cover at least part of the front surface of the housing and having an aperture positioned to correspond to the camera aperture in the front surface of the imaging box.

Example 23. A system comprising:

an imaging box for use in an image capture procedure for the performance assessment of a cleaning process, the imaging box comprising:

a housing defined by a front surface and a back surface and forming an interior cavity when the housing is placed on a substantially flat surface, the front surface having a receptacle configured to receive a mobile device, the front surface further including at least one camera aperture configured to correspond to the position of a camera lens of the mobile device when the mobile device is received in the receptacle, the back surface including a test strip slot configured to receive and hold a chemical test strip comprising a carrier and an indicator means in a substantially flat position, the back surface further including a test strip aperture configured to correspond to the position of a chemical test strip when received into the test strip slot, such that an image of the chemical test strip may be captured by the camera of the mobile device when the chemical test strip is inserted into the test strip slot such that the indicator means is facing the interior cavity of the housing;

a computing device configured to receive and evaluate the digital image of the chemical test strip and generate an assessment of the performance of the cleaning process; and a cleaning assessment application running on the mobile device configured to display the assessment of the performance of the cleaning process.

Example 24. The system of example 23 wherein the computing device is located remotely with respect to the mobile device.

Example 25. The system of example 23 wherein the application running on the mobile device is further configured to guide a user through a chemical test strip image capture procedure.

Example 26. The system of example 23, wherein the computing device is configured to evaluate the digital image of the chemical test strip according to:

c1) color-to-greyscale image data transformation;

c2) glare detection;

c3) greyscale-to binary image data transformation;

c4) image pixel-area normalization; and step c5) pixel-counting, wherein the number of black and white pixels of the test strip image data after the cleaning process are counted and the counting result is compared to the quantitative evaluation result of the test strip prior to the cleaning process.

Various examples have been described. These and other examples are within the scope of the following claims.

The invention claimed is:

1. A system comprising:

a computing device comprising:

one or more processors; and data storage storing processor-executable instructions, wherein execution of the processor-executable instructions by the one or more processors causes the one or more processors to:

guide a user through a test strip image capture procedure on the computing device;

perform an evaluation of an image of one or more test strips captured during the test strip image capture procedure after the one or more test strips have been exposed to a cleaning process;

generate an assessment of a performance of the cleaning process based on the evaluation, the one or more test strips including a carrier and an indicator operable to change as a function of the cleaning process;

select an action plan based on the assessment; and generate, for display on the computing device, the action plan selected based on the assessment.

2. The system of claim 1, wherein:

the one or more test strips include a plurality of indicators, wherein for each respective indicator of the plurality of indicators, the respective indicator corresponds to a respective parameter of a plurality of parameters of the cleaning process, the respective indicator is configured to change color independently of other indicators of the plurality of indicators as a function of the respective parameter corresponding to the respective indicator, and the one or more processors are configured to, as part of evaluating the image, determine color changes of the plurality of indicators.

3. The system of claim 2, wherein the one or more test strips includes a plurality of test strips, each test strip of the plurality of test strips including two or more indicators of the plurality of indicators.

4. The system of claim 2, wherein the one or more test strips consists of a single test strip.

5. The system of claim 2, wherein the one or more test strips includes a plurality of test strips, each indicator of the plurality of indicators being included in a different test strip of the plurality of test strips.

6. The system of claim 2, wherein the parameters correspond to different physical factors or chemical factors of the cleaning process.

7. The system of claim 2, wherein the parameters include one or more of:

spray pressure, a water hardness, water acidity, total dissolved solids, detergent dose, surfactant package, water temperature, presence and/or concentration of dissolved calcium, total or free chloride concentration, presence and/or concentration of an orthophosphate, m-alkalinity, p-alkalinity, presence and/or concentration of enzymes, presence and/or concentration of an anionic, non-ionic, or cationic tenside, presence and/or concentration of a corrosion inhibitor, presence and/or concentration of a polymer, presence and/or concentration of a biocide, or a combination of one or more other parameters.

8. The system of claim 1, wherein the action plan comprises one or more of:

advice to increase or lower a detergent concentration, advice to increase or lower a temperature, advice to increase or decrease a process time, advice to use a different detergent, or advice to change a water quality parameter.

9. The system of claim 1, wherein:

the computing device further comprises a camera, and the test strip image capture procedure comprises docking the computing device in an imaging box having a housing that defines a camera aperture configured to be aligned with the camera, the housing further comprising or defining a test strip slot configured to hold one or more test strip holders configured to hold the one or more test strips during image capture.

10. The system of claim 9, further comprising the imaging box.

11. The system of claim 1, wherein the computing device is a mobile phone device.

12. A method comprising:

outputting, by one or more processors of a computing device, for display on the computing device, guidance to guide a user through a test strip image capture procedure on the computing device;

performing, by the one or more processors, an evaluation of an image of one or more test strips captured during the test strip image capture procedure after the one or more test strips have been exposed to a cleaning process;

generating, by the one or more processors, an assessment of a performance of the cleaning process based on the evaluation, the one or more test strips including a carrier and an indicator operable to change as a function of the cleaning process;

selecting, by the one or more processors, an action plan based on the assessment; and generating, by the one or more processors, for display on the computing device, the action plan selected based on the assessment.

13. The method of claim 12, wherein:

the one or more test strips include a plurality of indicators, wherein for each respective indicator of the plurality of indicators, the respective indicator corresponds to a respective parameter of a plurality of parameters of the cleaning process, the respective indicator is configured to change color independently of other indicators of the plurality of indicators as a function of the respective parameter corresponding to the respective indicator, and evaluating the image comprises determining color changes of the plurality of indicators.

14. The method of claim 13, wherein the one or more test strips includes a plurality of test strips, each test strip of the plurality of test strips including two or more indicators of the plurality of indicators.

15. The method of claim 13, wherein the one or more test strips consists of a single test strip.

16. The method of claim 13, wherein the one or more test strips includes a plurality of test strips, each indicator of the plurality of indicators being included in a different test strip of the plurality of test strips.

17. The method of claim 13, wherein the parameters correspond to different physical factors or chemical factors of the cleaning process.

18. The method of claim 13, wherein the parameters include one or more of:

spray pressure,
a water hardness,
water acidity,
total dissolved solids,
detergent dose,
surfactant package,
water temperature,
presence and/or concentration of dissolved calcium,
total or free chloride concentration,
presence and/or concentration of an orthophosphate,
m-alkalinity,
p-alkalinity,
presence and/or concentration of enzymes,
presence and/or concentration of an anionic, non-ionic, or cationic tenside,
presence and/or concentration of a corrosion inhibitor,
presence and/or concentration of a polymer,
presence and/or concentration of a biocide, or
a combination of one or more other parameters.

19. The method of claim 12, wherein the action plan comprises one or more of:

advice to increase or lower a detergent concentration,
advice to increase or lower a temperature,
advice to increase or decrease a process time,
advice to use a different detergent, or
advice to change a water quality parameter.

20. The method of claim 12, wherein the test strip image capture procedure comprises docking the computing device in an imaging box having a housing that defines a camera aperture configured to be aligned with a camera of the computing device, the housing further comprising or defining a test strip slot configured to hold one or more test strip holders configured to hold the one or more test strips during image capture.

* * * * *